US005710004A

United States Patent [19]

Evans et al.

[11] Patent Number: 5,710,004
[45] Date of Patent: Jan. 20, 1998

[54] METHODS OF USING NOVEL STEROID HORMONE ORPHAN RECEPTORS

[75] Inventors: Ronald M. Evans, La Jolla; David J. Mangelsdorf, San Diego; Estelita S. Ong, San Diego; Anthony E. Oro, San Diego, all of Calif.; Uwe K. Borgmeyer, Hamburg, Germany; Vincent Giguere, Etobicoke, Canada; Tso-Pang Yao, San Diego, Calif.

[73] Assignee: The Salk Institute for Biological Studies, La Jolla, Calif.

[21] Appl. No.: 694,501

[22] Filed: Aug. 7, 1996

Related U.S. Application Data

[62] Division of Ser. No. 333,358, Nov. 2, 1994, Pat. No. 5,571,696, which is a continuation of Ser. No. 761,068, Sep. 17, 1991, abandoned.

[51] Int. Cl.[6] .............................. C12Q 1/68; C12P 21/06; C07K 14/00
[52] U.S. Cl. ......................... 435/6; 435/69.1; 435/69.4; 435/69.7; 435/325; 435/320.1; 536/23.1; 530/350
[58] Field of Search ........................ 435/6, 69.1, 69.4, 435/240.1, 320.1, 32, 5, 69.7; 536/23.1; 530/356, 300

[56] References Cited

U.S. PATENT DOCUMENTS

| | | | |
|---|---|---|---|
| 4,981,784 | 1/1991 | Evans et al. | 435/6 |
| 5,071,773 | 12/1991 | Evans et al. | 436/501 |
| 5,571,696 | 11/1996 | Evans | 435/69.1 |

OTHER PUBLICATIONS

Devereux et al., "A comprehensive set of sequence analysis programs for the VAX", Nucleic Acids Research vol. 12:387–395 (1984).

Kwok et al., "Nucleotide Sequence of a Full–Length Complementary DNA Clone and Amino Acid Sequence of Human Phenylalanine Hydroxylase," Biochemistry vol. 24:556–561 (1985).

Nathans et al., "Molecular Genetics of Human Color Vision: The Genes Encoding Blue, Green, and Red Pigments", Science vol. 232:193–202 (1986).

Hamada et al., "H–2RIIBP, a member of the nuclear hormone receptor superfamily that binds to both the regulatory element of major histocompatibility class I genes and the estrogen response element," Proc. Natl. Acad. Sci. USA vol. 86:8289–8293 (1989).

Tautz and Pfeifle, "A non–radioactive in situ hybridization method for the localization of specific RNAs in *Drosophila* embryos reveals translational control of the segmentation gene hunchback," Chromosoma vol. 98:81–85 (1989).

Giguere et al.,"Identification of a receptor for the morphogen retinoic acid," Nature vol. 330:624–629 (1987).

Evans, Ronald M., "The Steroid and Thyroid Hormone Receptor Superfamily," Science vol. 240:889–895.

Giguere et al., "Functional Domains of the Human Glucocorticoid Receptor," *Cell* 46: 645–652 (1986).

Giguere et al., "Identification of a new class of steroid hormone receptors," *Nature* 331: 91–94 (1988).

Court of Customs and Patent Appeals, in re Kirt and Petrow, Appl. No. 7522 Decided Mar. 16, 1967.

Primary Examiner—Karen C. Carlson
Attorney, Agent, or Firm—Gray Cary Ware & Freidenrich; Stephen E. Reiter

[57] ABSTRACT

Novel members of the steroid/thyroid superfamily of receptors are described. DNA sequences encoding same, expression vectors containing such DNA and host cells transformed with such expression vectors are also disclosed, as are methods for the expression of the novel receptors of the invention, and various uses thereof.

16 Claims, 1 Drawing Sheet

Correlation of XR1 Alternate Splicing Products

5,710,004

METHODS OF USING NOVEL STEROID HORMONE ORPHAN RECEPTORS

This application is a divisional of application Ser. No. 08/333,358, filed Nov. 2, 1994, now U.S. Pat. No. 5,571,696, which is a continuation of application Ser. No. 07/761,068, filed Sep. 17, 1991, now abandoned.

FIELD OF THE INVENTION

The present invention relates to novel steroid-hormone or steroid-hormone like receptor proteins, genes encoding such proteins, and methods of making and using such proteins. In a particular aspect, the present invention relates to bioassay systems for determining the selectivity of interaction between ligands and steroid-hormone or steroid-hormone like receptor proteins.

BACKGROUND OF THE INVENTION

Transcriptional regulation of development and homeostasis in complex eukaryotes, including humans and other mammals, birds, fish, insects, and the like, is controlled by a wide variety of regulatory substances, including steroid and thyroid hormones. These hormones exert potent effects on development and differentiation of phylogenetically diverse organisms. The effects of hormones are mediated by interaction with specific, high affinity binding proteins referred to as receptors.

The ability to identify additional compounds which are able to affect transcription of genes which are responsive to steroid hormones or metabolites thereof, would be of significant value in identifying compounds of potential therapeutic use. Further, systems useful for monitoring solutions, body fluids, and the like, for the presence of steroid hormones or metabolites thereof, would be of value in medical diagnosis, as well as for various biochemical applications.

A number of receptor proteins, each specific for one of several classes of cognate steroid hormones [e.g., estrogens (estrogen receptor), progesterones (progesterone receptor), glucocorticoid (glucocorticoid receptor), androgens (androgen receptor), aldosterones (mineralocorticoid receptor), vitamin D (vitamin D receptor)], retinoids (e.g., retinoic acid receptor) or for cognate thyroid hormones (e.g., thyroid hormone receptor), are known. Receptor proteins have been found to be distributed throughout the cell population of complex eukaryotes in a tissue specific fashion.

Molecular cloning studies have made it possible to demonstrate that receptors for steroid, retinoid and thyroid hormones are all structurally related and comprise a superfamily of regulatory proteins. These regulatory proteins are capable of modulating specific gene expression in response to hormone stimulation by binding directly to cis-acting elements. Structural comparisons and functional studies with mutant receptors have revealed that these molecules are composed of a series of discrete functional domains, most notably, a DNA-binding domain that is composed typically of 66–68 amino acids, including two zinc fingers and an associated carboxy terminal stretch of approximately 250 amino acids, which latter region comprises the ligand-binding domain.

An important advance in the characterization of this superfamily of regulatory proteins has been the delineation of a growing list of gene products which possess the structural features of hormone receptors. This growing list of gene products has been isolated by low-stringency hybridization techniques employing DNA sequences encoding previously identified hormone receptor proteins.

It is known that steroid or thyroid hormones, protected forms thereof, or metabolites thereof, enter cells and bind to the corresponding specific receptor protein, initiating an allosteric alteration of the protein. As a result of this alteration, the complex of receptor and hormone (or metabolite thereof) is capable of binding to certain specific sites on chromatin with high affinity.

It is also known that many of the primary effects of steroid and thyroid hormones involve increased transcription of a subset of genes in specific cell types.

A number of steroid hormone- and thyroid hormone-responsive transcriptional control units have been identified. These include the mouse mammary tumor virus 5'-long terminal repeat (MTV LTR), responsive to glucocorticoid, aldosterone and androgen hormones; the transcriptional control units for mammalian growth hormone genes, responsive to glucocorticoids, estrogens and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic $\alpha_{2u}$-globulin gene transcriptional control units, responsive to androgens, estrogens, thyroid hormones, and glucocorticoids.

A major obstacle to further understanding and more widespread use of the various members of the steroid/thyroid superfamily of hormone receptors has been a lack of availability of the receptor proteins, in sufficient quantity and sufficiently pure form, to allow them to be adequately characterized. The same is true for the DNA gene segments which encode them. Lack of availability of these DNA segments has prevented in vitro manipulation and in vivo expression of the receptor-encoding genes, and consequently the knowledge such manipulation and expression would yield.

In addition, a further obstacle to a more complete understanding and more widespread use of members of the steroid/thyroid receptor superfamily is the fact that additional members of this superfamily remain to be discovered, isolated and characterized.

The present invention is directed to overcoming these problems of short supply of adequately purified receptor material, lack of DNA segments which encode such receptors and increasing the number of identified and characterized hormone receptors which are available for use.

BRIEF DESCRIPTION OF THE INVENTION

In accordance with the present invention, we have discovered novel members of the steroid/thyroid superfamily of receptors. The novel receptors of the present invention are soluble, intracellular, nuclear (as opposed to cell surface) receptors, which are activated to modulate transcription of certain genes in animal cells when the cells are exposed to ligands therefor. The nuclear receptors of the present invention differ significantly from known steroid receptors, both in primary sequence and in responsiveness to exposure of cells to various ligands, e.g., steroids or steroid-like compounds.

Also provided in accordance with the present invention are DNAs encoding the receptors of the present invention, including expression vectors for expression thereof in animal cells, cells transformed with such expression vectors, cells co-transformed with such expression vectors and reporter vectors (to monitor the ability of the receptors to modulate transcription when the cells are exposed to a compound which interacts with the receptor); and methods of using such co-transformed cells in screening for compounds which are capable of leading to modulation of receptor activity.

Further provided in accordance with the present invention are DNA and RNA probes for identifying DNAs encoding additional steroid receptors.

In accordance with yet another embodiment of the invention, there is provided a method for making the receptors of the invention by expressing DNAs which encode the receptors in suitable host organisms.

The novel receptors and DNAs encoding same can be employed for a variety of purposes. For example, novel receptors of the present invention can be included as part of a panel of receptors which are screened to determine the selectivity of interaction of proposed agonists or antagonists and other receptors. Thus, a compound which is believed to interact selectively, for example, with the glucocorticoid receptor, should not have any substantial effect on any other receptors, including those of the present invention. Conversely, if such a proposed compound does interact with one or more of the invention receptors, then the possibility of side reactions caused by such compound is clearly indicated.

DETAILED DESCRIPTION OF THE INVENTION

Figure 1:
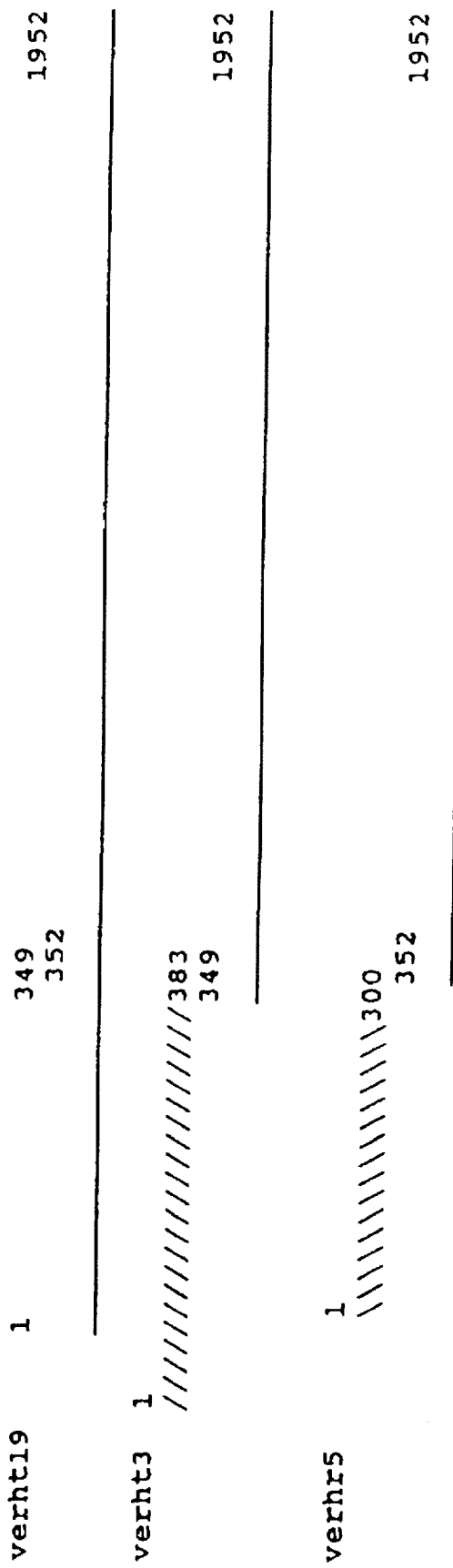
FIG. 1 is a schematic diagram correlating the relationship between the alternate spliced variants of invention receptor XR1.

In accordance with the present invention, there are provided DNAs encoding a polypeptide characterized by having a DNA binding domain comprising about 66 amino acids with 9 cysteine (Cys) residues, wherein said DNA binding domain has:

(i) less than about 70% amino acid sequence identity with the DNA binding domain of human retinoic acid receptor-alpha (hRAR-alpha);

(ii) less than about 60% amino acid sequence identity with the DNA binding domain of human thyroid receptor-beta (hTR-beta);

(iii) less than about 50% amino acid sequence identity with the DNA binding domain of human glucocorticoid receptor (hGR); and (iv) less than about 65% amino acid sequence identity in with the DNA binding domain of human retinoid X receptor-alpha (hRXR-alpha).

Alternatively, DNAs of the invention can be characterized with respect to percent amino acid sequence identity of the ligand binding domain of polypeptides encoded thereby, relative to amino acid sequences of previously characterized receptors. As yet another alternative, DNAs of the invention can be characterized by the percent overall amino acid sequence identity of polypeptides encoded thereby, relative to amino acid sequences of previously characterized receptors.

Thus, DNAs of the invention can be characterized as encoding polypeptides having, in the ligand binding domain:

(i) less than about 35% amino acid sequence identity with the ligand binding domain of hRAR-alpha;

(ii) less than about 30% amino acid sequence identity with the ligand binding domain of hTR-beta;

(iii) less than about 25% amino acid sequence identity with the ligand binding domain of hGR; and (iv) less than about 30% amino acid sequence identity with the ligand binding domain of hRXR-alpha.

DNAs of the invention can be further characterized as encoding polypeptides having an overall amino acid sequence identity of:

(i) less than about 35% relative to hRAR-alpha;

(ii) less than about 35% relative to hTR-beta;

(iii) less than about 25% relative to hGR; and (iv) less than about 35% relative to hRXR-alpha.

Specific receptors contemplated for use in the practice of the present invention include:

"XR1" (variously referred to herein as receptor "XR1", "hXR1", "hXR1.pep" or "verHT19.pep"; wherein the prefix "h" indicates the clone is of human origin), a polypeptide characterized as having a DNA binding domain comprising:

(i) about 68% amino acid sequence identity with the DNA binding domain of hRAR-alpha;

(ii) about 59% amino acid sequence identity with the DNA binding domain of hTR-beta;

(iii) about 45% amino acid sequence identity with the DNA binding domain of hGR; and (iv) about 65% amino acid sequence identity with the DNA binding domain of hRXR-alpha;

see also Sequence ID No. 2 for a specific amino acid sequence representative of XR1, as well as Sequence ID No. 1 which is an exemplary nucleotide sequence encoding XR1. In addition, Sequence ID Nos. 4 and 6 present alternate amino terminal sequences for the clone referred to as XR1 (the variant referred to as verht3 is presented in Sequence ID No. 4 (an exemplary nucleotide sequence encoding such variant presented in Sequence ID No. 3), and the variant referred to as verhr5 is presented in Sequence ID No. 6 (an exemplary nucleotide sequence encoding such variant presented in Sequence ID No. 5);

"XR2" (variously referred to herein as receptor "XR2", "hXR2" or "hXR2.pep"), a polypeptide characterized as having a DNA binding domain comprising:

(i) about 55% amino acid sequence identity with the DNA binding domain of hRAR-alpha;

(ii) about 56% amino acid sequence identity with the DNA binding domain of hTR-beta;

(iii) about 50% amino acid sequence identity with the DNA binding domain of hGR; and (iv) about 52% amino acid sequence identity with the DNA binding domain of hRXR-alpha;

see also Sequence ID No. 8 for a specific amino acid sequence representative of XR2, as well as Sequence ID No. 7 which is an exemplary nucleotide sequence encoding XR2;

"XR4" (variously referred to herein as receptor "XR4", "mXR4" or "mXR4.pep"; wherein the prefix "m" indicates the clone is of mouse origin), a polypeptide characterized as having a DNA binding domain comprising:

(i) about 62% amino acid sequence identity with the DNA binding domain of hRAR-alpha;

(ii) about 58% amino acid sequence identity with the DNA binding domain of hTR-beta;

(iii) about 48% amino acid sequence identity with the DNA binding domain of hGR; and (iv) about 62% amino acid sequence identity with the DNA binding domain of hRXR-alpha;

see also Sequence ID No. 10 for a specific amino acid sequence representative of XR4, as well as Sequence ID No. 9 which is an exemplary nucleotide sequence encoding XR4;

"XR5" (variously referred to herein as receptor "XR5", "mXR5" or "mXR5.pep"), a polypeptide characterized as having a DNA binding domain comprising:
  (i) about 59% amino acid sequence identity with the DNA binding domain of hRAR-alpha;
  (ii) about 52% amino acid sequence identity with the DNA binding domain of hTR-beta;
  (iii) about 44% amino acid sequence identity with the DNA binding domain of hGR; and
  (iv) about 61% amino acid sequence identity with the DNA binding domain of hRXR-alpha;

see also Sequence ID No. 12 for a specific amino acid sequence representative of XR5, as well as Sequence ID No. 11 which is an exemplary nucleotide sequence encoding XR5; and "XR79" (variously referred to herein as "XR79", "dXR79" or "dXR79.pep"; wherein the prefix "d" indicates the clone is of Drosophila origin), a polypeptide characterized as having a DNA binding domain comprising:
  (i) about 59% amino acid sequence identity with the DNA binding domain of hRAR-alpha;
  (ii) about 55% amino acid sequence identity with the DNA binding domain of hTR-beta;
  (iii) about 50% amino acid sequence identity with the DNA binding domain of hGR; and
  (iv) about 65% amino acid sequence identity with the DNA binding domain of hRXR-alpha;

see also Sequence ID No. 14 for a specific amino acid sequence representative of XR79, as well as Sequence ID No. 13 which is an exemplary nucleotide sequence encoding XR79.

The receptor referred to herein as "XR1" is observed as three closely related proteins, presumably produced by alternate splicing from a single gene. The first of these proteins to be characterized (referred to as "verht19") comprises about 548 amino acids, and has a $M_r$ of about 63 kilodalton. Northern analysis indicates that a single mRNA species corresponding to XR1 is highly expressed in the brain. A variant of verht19 (alternatively referred to as "verht3", XR1 or XR1prime) is further characterized as comprising about 556 amino acids, and having a $M_r$ of about 64 kilodalton. Yet another variant of verht19 (alternatively referred to as "verhr5", XR1" or XR1prim2) is further characterized as comprising about 523 amino acids, and having a $M_r$ of about 60 kilodalton. The interrelationship between these three variants of XR1 is illustrated schematically in FIG. 1.

The receptor referred to herein as "XR2" is further characterized as a protein comprising about 440 amino acids, and having a $M_r$ of about 50 kilodalton. Northern analysis indicates that a single mRNA species (~1.7 kb) corresponding to XR2 is expressed most highly in liver, kidney, lung, intestine and adrenals of adult male rats. Transactivation studies (employing chimeric receptors containing the XR2 DNA binding domain and the ligand binding domain of a prior art receptor) indicate that XR2 is capable of binding to $TRE_{pal}$. In terms of amino acid sequence identity with prior art receptors, XR2 is most closely related to the vitamin D receptor (39% overall amino acid sequence identity, 17% amino acid identity in the amino terminal domain of the receptor, 53% amino acid identity in the DNA binding domain of the receptor and 37% amino acid identity in the ligand binding domain of the receptor).

The receptor referred to herein as "XR4" is further characterized as a protein comprising about 439 amino acids, and having a $M_r$ of about 50 kilodalton. In terms of amino acid sequence identity with prior art receptors, XR4 is most closely related to the peroxisome proliferator-activated receptor (62% overall amino acid sequence identity, 30% amino acid identity in the amino terminal domain of the receptor, 86% amino acid identity in the DNA binding domain of the receptor and 64% amino acid identity in the ligand binding domain of the receptor). XR4 is expressed ubiquitously and throughout development (as determined by in situ hybridization).

The receptor referred to herein as "XR5" is further characterized as a protein comprising about 556 amino acids, and having a $M_r$ of about 64 kilodalton. In situ hybridization reveals widespread expression throughout development. High levels of expression are observed in the embryonic liver around day 12, indicating a potential role in haematopoiesis. High levels are also found in maturing dorsal root ganglia and in the skin. In terms of amino acid sequence identity with prior art receptors, XR5 most closely related to the rat nerve growth factor induced protein-B (NGFI-B) receptor. With respect to NGFI-B, XR5 has 29% overall amino acid sequence identity, 15% amino acid identity in the amino terminal domain of the receptor, 52% amino acid identity in the DNA binding domain of the receptor and 29% amino acid identity in the ligand binding domain of the receptor.

The receptor referred to herein as "XR79" is further characterized as a protein comprising about 601 amino acids, and having a $M_r$ of about 66 kilodalton. Whole mount in situ hybridization reveals a fairly uniform pattern of RNA expression during embryogenesis. Northern blot analysis indicates that a 2.5 kb transcript corresponding to XR79 is present in RNA throughout development. The levels of XR79 mRNA are highest in RNA from 0–3 hour old embryos, i.e., maternal product, and lowest in RNA from the second instar larvae (L2 stage). In situ hybridization reveals that XR79 is distributed relatively uniformly at different stages of embryogenesis. In terms of amino acid sequence identity with prior art receptors, XR79 is most closely related to the mammalian receptor TR2 [see Chang and Kokontis in Biochemical and Biophysical Research Communications 155: 971–977 (1988)], as well as members of the coup family, i.e., ear2, coup(ear3), harp-1. With respect to TR2, XR79 has 33% overall amino acid sequence identity, 16% amino acid identity in the amino terminal domain of the receptor, 74% amino acid identity in the DNA binding domain of the receptor and 28% amino acid identity in the ligand binding domain of the receptor. With respect to coup (ear3) [see Miyajima et al., in Nucl Acids Res 16: 11057–11074 (1988)], XR79 has 32% overall amino acid sequence identity, 21% amino acid identity in the amino terminal domain of the receptor, 62% amino acid identity in the DNA binding domain of the receptor and 22% amino acid identity in the ligand binding domain of the receptor.

In accordance with a specific embodiment of the present invention, there is provided an expression vector which comprises DNA as previously described (or functional fragments thereof), and which further comprises:
  at the 5'-end of said DNA, a promoter and a nucleotide triplet encoding a translational start codon, and
  at the 3'-end of said DNA, a nucleotide triplet encoding a translational stop codon;
wherein said expression vector is operative in a cell in culture (e.g., yeast, bacteria, mammalian) to express the protein encoded by said DNA.

As employed herein, reference to "functional fragments" embraces DNA encoding portions of the invention receptors which retain one or more of the functional characteristics of steroid hormone or steroid hormone-like receptors, e.g., DNA binding properties of such receptors, ligand binding properties of such receptors, the ability to heterodimerize, nuclear localization properties of such receptors, phosphorylation properties of such receptors, transactivation domains characteristic of such receptors, and the like.

In accordance with a further embodiment of the present invention, there are provided cells in culture (e.g., yeast, bacteria, mammalian) which are transformed with the above-described expression vector.

In accordance with yet another embodiment of the present invention, there is provided a method of making the above-described novel receptors (or functional fragments thereof) by culturing the above-described cells under conditions suitable for expression of polypeptide product.

In accordance with a further embodiment of the present invention, there are provided novel polypeptide products produced by the above-described method.

In accordance with a still further embodiment of the present invention, there are provided chimeric receptors comprising at least an amino-terminal domain, a DNA-binding domain, and a ligand-binding domain, wherein at least one of the domains thereof is derived from the novel polypeptides of the present invention; and wherein at least one of the domains thereof is derived from at least one previously identified member of the steroid/thyroid superfamily of receptors e.g., glucocorticoid receptor (GR), thyroid receptors (TR), retinoic acid receptors (RAR), mineralocorticoid receptor (MR), estrogen receptor (ER), the estrogen related receptors (e.g., hERR1 or hERR2), retinoid X receptors (e.g., RXRα, RXRβ or RXRδ), vitamin D receptor (VDR), aldosterone receptor (AR), progesterone receptor (PR), the ultraspiracle receptor (USP), nerve growth factor induced protein-B (NGFI-B), the coup family of transcription factors (COUP), peroxisome proliferator-activated receptor (PPAR), mammalian receptor TR2 (TR2), and the like.

In accordance with yet another embodiment of the present invention, there is provided a method of using polypeptides of the invention to screen for response elements and/or ligands for the novel receptors described herein. The method to identify compounds which act as ligands for receptor polypeptides of the invention comprising:

assaying for the presence or absence of reporter protein upon contacting of cells containing a chimeric form of said receptor polypeptide and reporter vector with said compound;

wherein said chimeric form of said receptor polypeptide comprises the ligand binding domain of said receptor polypeptide and the amino-terminal and DNA-binding domains of one or more previously identified members of the steroid/thyroid superfamily of receptors;

wherein said reporter vector comprises:
  (a) a promoter that is operable in said cell,
  (b) a hormone response element which is responsive to the receptor from which the DNA-binding domain of said chimeric form of said receptor polypeptide is derived, and
  (c) a DNA segment encoding a reporter protein,
    wherein said reporter protein-encoding DNA segment is operatively linked to said promoter for transcription of said DNA segment, and
    wherein said hormone response element is operatively linked to said promoter for activation thereof, and thereafter identifying those compounds which induce or block the production of reporter in the presence of said chimeric form of said receptor polypeptide.

The method to identify response elements for receptor polypeptides of the invention comprises:

assaying for the presence or absence of reporter protein upon contacting of cells containing a chimeric form of said receptor polypeptide and reporter vector with a compound which is a known agonist or antagonist for the receptor from which the ligand-binding domain of said chimeric form of said receptor polypeptide is derived;

wherein said chimeric form of said receptor polypeptide comprises the DNA-binding domain of the receptor polypeptide and the amino-terminal and ligand-binding domains of one or more previously identified members of the steroid/thyroid superfamily of receptors;

wherein said reporter vector comprises:
  (a) a promoter that is operable in said cell,
  (b) a putative hormone response element, and
  (c) a DNA segment encoding a reporter protein,
    wherein said reporter protein-encoding DNA segment is operatively linked to said promoter for transcription of said DNA segment, and
    wherein said hormone response element is operatively linked to said promoter for activation thereof; and identifying those response elements for which the production of reporter is induced or blocked in the presence of said chimeric form of said receptor polypeptide.

In accordance with yet another embodiment of the present invention, there is provided a DNA or RNA labeled for detection; wherein said DNA or RNA comprises a nucleic acid segment, preferably of at least 20 bases in length, wherein said segment has substantially the same sequence as a segment of the same length selected from the DNA segment represented by bases 21–1902, inclusive, of Sequence ID No. 1, bases 1–386, inclusive, of Sequence ID No. 3, bases 10–300, inclusive, of Sequence ID No. 5, bases 21–1615, inclusive, of Sequence ID No. 7, bases 21–2000, inclusive, of Sequence ID No. 9, bases 1–2450, inclusive, of Sequence ID No. 11, bases 21–2295, inclusive, of Sequence ID No. 13, or the complement of any of said segments.

In accordance with still another embodiment of the present invention, there are provided methods of testing compound(s) for the ability to regulate transcription-activating effects of a receptor polypeptide, said method comprising assaying for the presence or absence of reporter protein upon contacting of cells containing a receptor polypeptide and reporter vector with said compound;

wherein said receptor polypeptide is characterized by having a DNA binding domain comprising about 66 amino acids with 9 Cys residues, wherein said DNA binding domain has:
  (i) less than about 70% amino acid sequence identity with the DNA binding domain of hRAR-alpha;
  (ii) less than about 60% amino acid sequence identity with the DNA binding domain of hTR-beta;
  (iii) less than about 50% amino acid sequence identity with the DNA binding domain of hGR; and
  (iv) less than about 65% amino acid sequence identity with the DNA binding domain of hRXR-alpha; and wherein said reporter vector comprises:
  (a) a promoter that is operable in said cell,
  (b) a hormone response element, and
  (c) a DNA segment encoding a reporter protein, wherein said reporter protein-encoding DNA segment is operatively linked to said promoter for transcription of said DNA segment, and wherein said hormone response element is operatively linked to said promoter for activation thereof.

In accordance with a still further embodiment of the present invention, there is provided a method of testing a compound for its ability to selectively regulate the transcription-activating effects of a specific receptor polypeptide, said method comprising:

assaying for the presence or absence of reporter protein upon contacting of cells containing said receptor polypeptide and reporter vector with said compound;

wherein said receptor polypeptide is characterized by being responsive to the presence of a known ligand for said receptor to regulate the transcription of associated gene(s);

wherein said reporter vector comprises:
(a) a promoter that is operable in said cell,
(b) a hormone response element, and
(c) a DNA segment encoding a reporter protein,
wherein said reporter protein-encoding DNA segment is operatively linked to said promoter for transcription of said DNA segment, and
wherein said hormone response element is operatively linked to said promoter for activation thereof; and assaying for the presence or absence of reporter protein upon contacting of cells containing chimeric receptor polypeptide and reporter vector with said compound;

wherein said chimeric receptor polypeptide comprises the ligand binding domain of a novel receptor of the present invention, and the DNA binding domain of said specific receptor; and thereafter selecting those compounds which induce or block the production of reporter in the presence of said specific receptor, but are substantially unable to induce or block the production of reporter in the presence of said chimeric receptor.

The above-described methods of testing compounds for the ability to regulate transcription-activating effects of invention receptor polypeptides can be carried out employing methods described in U.S. Ser. No. 108,471, filed Oct. 20, 1987, the entire contents of which are hereby incorporated by reference herein.

As employed herein, the term "expression vector" refers to constructs containing DNA of the invention (or functional fragments thereof), plus all sequences necessary for manipulation and expression of such DNA. Such an expression vector will contain both a "translational start site" and a "translational stop site". Those of skill in the art can readily identify sequences which act as either translational start sites or translational stop sites.

Suitable host cells for use in the practice of the present invention include prokaroytic and eukaryote cells, e.g., bacteria, yeast, mammalian cells and the like.

Labeled DNA or RNA contemplated for use in the practice of the present invention comprises nucleic acid sequences covalently attached to readily analyzable species such as, for example, radiolabel (e.g., $^{32}P$, $^{3}H^{35}S$, and the like), enzymatically active label, and the like.

The invention will now be described in greater detail by reference to the following non-limiting examples.

EXAMPLES

Example I

ISOLATION AND CHARACTERIZATION OF XR1

The KpnI/SacI restriction fragment (503 bp) including the DNA-binding domain of hRAR-alpha-encoding DNA [See Giguere et al., Nature 330: 624–629 (1987); and commonly assigned U.S. patent application Ser. No. 276,536, filed Nov. 30, 1988; and European Patent Application Publication No. 0 325 849, all incorporated herein by reference] was nick-translated and used to screen a rat brain cDNA library [see DNA Cloning, A practical approach, Vol I and II, D. M. Glover, ed. (IRL Press (1985)] and a lambda-gt11 human liver cDNA library [Kwok et al., Biochem. 24: 556 (1985)] at low stringency. The hybridization mixture contained 35% formamide, 1× Denhardt's, 5× SSPE (1× SSPE=0.15M NaCl mM $Na_2HPO_4$ 1 mM EDTA), 0.1% SDS, 10% dextran sulfate, 100 µg/ml denatured salmon sperm DNA and $10^6$ cpm of [P]-labelled probe. Duplicate nitrocellulose filters were hybridized for 16h at 42° C., washed once at 25° C. for 15 min with 2×SSC (1× SSC=0.15M NaCl, 0.015M sodium citrate), 0.1% SDS and then washed twice at 55° C. for 30 min. in 2×SSC, 0.1% SDS. The filters were autoradiographed for 3 days at −70° C. using an intensifying screen.

After several rounds of screening, a pure positive clone having an insert of about 2.1 kb is obtained from the rat brain cDNA library. Several positive clones are obtained from the human liver library. Sequence analysis of the positive rat brain clone indicates that this clone encodes a novel member of the steroid/thyroid superfamily of receptors. Sequence analysis of one of the positive human liver clones (designated "hL1", a 1.7 kb cDNA) indicates that this clone is the human equivalent of the rat brain clone, based on sequence homology.

The EcoRI insert of clone hL1 (labeled with $^{32}P$ is also used as a probe to screen a human testis cDNA library (Clonetech) and a human retina cDNA library [see Nathans et al., in Science 232: 193–202 (1986)]. Hybridization conditions comprised a hybridization mixture containing 50% formamide, 1× Denhardt's, 5× SSPE, 0.1% SDS, 100 µg/ml denatured salmon sperm DNA and 106 cpm of [$^{32}P$]-labelled probe. Duplicate nitrocellulose filters were hybridized for 16h at 42° C., washed once at 25° C. for 15 min with 2× SSC (1× SSC=0.015M NaCl, 0.015M sodium citrate), 0.1% SDS and then washed twice at 55° C. for 30 min. in 2× SSC, 0.1% SDS. The filters were autoradiographed for 3 days at −70° C. using an intensifying screen.

After several rounds of screening, five (5) positive clones were obtained from the human retina cDNA library, and five (5) positive clones were obtained from the human testis cDNA library. Sequence analysis of two clones from the testis library indicates that these clones encode different isoforms of the same novel member of the steroid/thyroid superfamily of receptors (designated as "Verht19" and "Verht3"). Sequence analysis of one of the positive clones from the human retina library indicates that this clone is yet another isoform of the same novel member of the steroid/thyroid superfamily of receptors (designated "Verhr5"). The full length sequence of Verht19 is set forth herein as Sequence ID No. 1 (which includes an indication of where the splice site is for each of the variants, verht3 and verhr5). The amino-terminal sequence of verht3 and verhr5 are presented in Sequence ID Nos. 3 and 5, respectively. In addition, the interrelationship between each of these three isoforms is illustrated schematically in FIG. 1.

Example II

ISOLATION AND CHARACTERIZATION OF XR2

The KpnI/SacI restriction fragment (503 bp) including the DNA-binding domain of hRAR-alpha-encoding DNA [See Giguere et al., Nature 330: 624 (1987); and commonly assigned U.S. patent application Ser. No. 276,536, filed Nov. 30, 1988; and European Patent Application Publication No. 0 325 849, all incorporated herein by reference] was nick-translated and used to screen a lambda-gt11 human liver cDNA library [Kwok et al., Biochem. 24: 556 (1985)] at low stringency. The hybridization mixture contained 35% formamide, 1× Denhardt's, 5× SSPE (1× SSPE=0.15M NaCl, 10 mM $Na_2HPO_4$, 1 mM EDTA), 0.1% SDS, 10% dextran sulfate, 100 mg/ml denatured salmon sperm DNA and $10^6$ cpm of [P]-labelled probe. Duplicate nitrocellulose filters were hybridized for 16h at 42° C., washed once at 25° C. for 15 min with 2× SSC (1× SSC=0.15M NaCl, 0.015M sodium citrate), 0.1% SDS and then washed twice at 55° C. for 30 min. in 2× SSC, 0.1% SDS. The filters were autoradiographed for 3 days at −70° C. using an intensifying screen.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs [Devereux et al., Nucl. Acids Res. 12, 387 (1984)]. Several clones of a unique receptor-like sequence were identified, the longest of which was designated lambda-HL1-1 (also referred to herein as XR2).

The DNA sequence of the resulting clone is set forth as Sequence ID No. 7.

Example III

ISOLATION AND CHARACTERIZATION OF XR4

A clone which encodes a portion of the coding sequence for XR4 was isolated from a mouse embryonic library by screening under low stringency conditions (as described above).

The library used was a lambda gt10 day 8.5 cDNA library having an approximate titer of 1.3×10/ml (derived from 8.5 day old embryonic material with as much of the amnion and extraembryonic tissues dissected away as possible). This library was prepared from poly $A^+$ selected RNA (by oligo-dT priming), Gubler & Hoffman cloning methods [Gene 25: 263 (1983)], and cloned into the EcoRI site of lambda gt10.

The probe used was a mixture of radioactively labeled DNA derived from the DNA binding regions of the human alpha and beta retinoic acid receptors.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs [Devereux et al., Nucl. Acids Res. 12, 387 (1984)]. Several clones of a unique receptor-like sequence were identified, the longest of which was designated XR4.

The DNA sequence of the resulting clone is set forth as Sequence ID No. 9.

Example IV

ISOLATION AND CHARACTERIZATION OF XR5

A clone which encodes a portion of the coding sequence for XR5 was isolated from a mouse embryonic library by screening under low stringency conditions (as described above).

The library used was the same lambda gt10 day 8.5 cDNA library described in the preceding example. Similarly, the probe used was the same mixture of radioactively labeled DNA described in the preceding example.

Only one of the clones isolated corresponds to a portion of the coding region for XR5. A 0.7 kb EcoRI fragment of this clone (designated as No. II-17) was subcloned into the bluescript pksII-Vector. Partial sequence analysis of this insert fragment shows homology to the DNA binding domain of the retinoic acid receptors.

The EcoRI-insert was used to rescreen a second library (a mouse lambda ZAPII day 6.5 cDNA library, prepared as described below) under high stringency conditions. A total of 21 phages were isolated and rescued into the psk-vector. Partial sequencing allowed inserts from 13 of these phages to be identified as having sequences which overlap with XR5 II-17. The clone with the longest single EcoRI-insert was sequenced, revealing an open reading frame of 556 amino acids. This sequence was extended further upstream by 9 bp from the furthest 5'-reaching clone.

The DNA sequence of the resulting clone is set forth as Sequence ID No. 11.

The day 6.5 cDNA library, derived from 6.5 day old mouse embryonic material was prepared from poly selected RNA (by oligo-dT priming), and cloned into the EcoRI site of lambda gt10.

Example V

ISOLATION AND CHARACTERIZATION OF XR79

The 550 bp BamHI restriction fragment, including the DNA-binding domain of mouse RAR-beta-encoding DNA (See Hamada et al., Proc. Natl. Acad. Sci. 86: 8289 (1989); incorporated by reference herein) was nick-translated and used to screen a Lambda-ZAP cDNA library comprising a size selected Drosophila genomic library (~2–5 kb, EcoRI restricted) at low stringency. The hybridization mixture contained 35% formamide, 1× Denhardt's, 5× SSPE (1× SSPE=0.15M NaCl, 10mM $Na_2HPO_4$,1 mM EDTA), 0.1% SDS, 10% dextran sulfate, 100 mg/ml denatured salmon sperm DNA and $10^6$ cpm of [$^{32}$P]-labelled probe. Duplicate nitrocellulose filters were hybridized for 16h at 42° C., washed once at 25° C. for 15 min with 2× SSC (1× SSC=0.15M NaCl,0.015M sodium citrate), 0.1% SDS and then washed twice at 55° C. for 30 min. in 2× SSC, 0.1% SDS. The filters were autoradiographed for 3 days at −70° C. using an intensifying screen.

After several rounds of screening, a pure positive clone having an insert of about 3.5 kb is obtained from the Drosophila genomic library. This genomic clone was then used to screen a Drosophila imaginal disc lambda gt10 cDNA library [obtained from Dr. Charles Zuker; see DNA Cloning, A practical approach, Vol I and II, D. M. Glover, ed. (IRL Press (1985)]. Hybridization conditions comprised a hybridization mixture containing 50% formamide, 1× Denhardt's, 5× SSPE, 0.1% SDS, 100 µg/ml denatured salmon sperm DNA and $10^6$ cpm of [P]-labelled probe. Duplicate nitrocellulose filters were hybridized for 16h at 42° C., washed once at 25° C. for 15 min with 2× SSC (1× SSC=0.15M NaCl, 0.015M sodium citrate), 0.1% SDS and then washed twice at 55° C. for 30 min. in 2× SSC, 0.1% SDS. The filters were autoradiographed for 3 days at −70° C. using an intensifying screen.

Sequence analysis of the positive cDNA clone indicates that this clone encodes another novel member of the steroid/ thyroid superfamily of receptors (designated "XR79" a 2.5 kb cDNA) See Sequence ID No. 13 for the DNA sequence of the resulting clone.

The 2.5 kbcDNA encoding XR79 was nick-translated and used as a probe for a nitrocellulose filter containing size-fractionated total RNA, isolated by standard methods from Drosophila melanogaster of different developmental stages. The probe hybridized to a 2.5 kb transcript which was present in RNA throughout development. The levels were highest in RNA from 0–3 hour old embryos and lowest in RNA from second instar larvae. The same 2.5 kb cDNA was nick translated using biotinylated nucleotides and used as a probe for in situ sybridization to whole Drosophila embryos [Tautz and Pfeifle, Chromosoma 98: 81–85 (1989)]. The RNA distribution appeared relatively uniform at different stages of embryogenesis.

Example VI

SEQUENCE COMPARISONS OF INVENTION RECEPTORS WITH hRARα, hTRβ, hGR, AND hRXRα

Amino acid sequences of XR1, hRAR-alpha (human retinoic acid receptor-alpha), hTR-beta (human thyroid hormone receptor-beta), hGR (human glucocorticoid receptor), and hRXR-alpha (human retinoid receptor-alpha) were aligned using the University of Wisconsin Genetics Computer Group program "Bestfit" (Devereux et al., supra). The percentage of amino acid identity between RX2 and the other receptors, i.e., in the 66–68 amino acid DNA binding domains and the ligand-binding domains, are summarized in Table 1 as percent amino acid identity.

TABLE 1

Percent amino acid identity between receptor XR1 (verht19) and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 18 | 21 | 45 | 20 |
| hTRβ | 31 | 14 | 59 | 30 |
| hRARα | 32 | 25 | 68 | 27 |
| hRXRα | 29 | 15 | 65 | 22 |

[1]"N-term" = amino terminal domain
[2]"DNA-BD" = receptor DNA binding domain
[3]"Ligand-BD" = receptor ligand binding domain Similarly, the amino acid sequences of invention receptors XR2, XR4, XR5, and XR79 were compared with human RAR-alpha (hRARα), human TR-beta (hTRβ), human glucocorticoid (hGR) and human RXR-alpha (hRXRα). As done in Table 1, the percentage of amino acid identity between the invention receptors and the other receptors are summarized in Tables 2–5, respectively.

TABLE 2

Percent amino acid identity between receptor XR2 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 24 | 21 | 50 | 20 |
| hTRβ | 31 | 19 | 56 | 29 |
| hRARα | 33 | 21 | 55 | 32 |
| hRXRα | 27 | 19 | 52 | 23 |

[1]"N-term" = amino terminal domain
[2]"DNA-BD" = receptor DNA binding domain
[3]"Ligand-BD" = receptor ligand binding domain

TABLE 3

Percent amino acid identity between receptor XR4 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 25 | 24 | 48 | 21 |
| hTRβ | 31 | 21 | 58 | 27 |
| hRARα | 32 | 22 | 62 | 29 |
| hRXRα | 33 | 24 | 62 | 28 |

[1]"N-term" = amino terminal domain
[2]"DNA-BD" = receptor DNA binding domain
[3]"Ligand-BD" = receptor ligand binding domain

TABLE 4

Percent amino acid identity between receptor XR5 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 20 | 20 | 44 | 20 |
| hTRβ | 24 | 14 | 52 | 22 |
| hRARα | 27 | 19 | 59 | 19 |
| hRXRα | 29 | 17 | 61 | 27 |

[1]"N-term" = amino terminal domain
[2]"DNA-BD" = receptor DNA binding domain
[3]"Ligand-BD" = receptor ligand binding domain

TABLE 5

Percent amino acid identity between receptor XR79 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 18 | 22 | 50 | 20 |
| hTRβ | 28 | 22 | 55 | 20 |
| hRARα | 24 | 14 | 59 | 18 |
| hRXRα | 33 | 20 | 65 | 24 |

[1]"N-term" = amino terminal domain
[2]"DNA-BD" = receptor DNA binding domain
[3]"Ligand-BD" = receptor ligand binding domain While the invention has been described in detail with reference to certain preferred embodiments thereof, it will be understood that modifications and variations are within the spirit and scope of that which is described and claimed.

SUMMARY OF SEQUENCES

Sequence ID No. 1 is a nucleotide sequence encoding novel receptor of the present invention designated as "hXR1".

Sequence ID No. 2 is the amino acid sequence deduced from the nucleotide sequence set forth in Sequence ID No. 1 (variously referred to herein as receptor "XR1", "hXR1", "hXR1.pep" or "verHT19.pep").

Sequence ID No. 3 is a nucleotide sequence encoding the amino-terminal portion of the novel receptor of the present invention designated as "hXR1prime".

Sequence ID No. 4 is the amino acid sequence deduced from the nucleotide sequence set forth in Sequence ID No. 3 (variously referred to herein as receptor "XR1prime", "hXR1prime", "hXR1prime.pep" or "verHT3.pep").

Sequence ID No. 5 is a nucleotide sequence encoding the amino-terminal portion of the novel receptor of the present invention designated as "hXR1prim2".

Sequence ID No. 6 is the amino acid sequence deduced from the nucleotide sequence set forth in Sequence ID No. 5 (variously referred to herein as receptor " XR1prim2", "hXR1prim2", " hXR1prim2.pep"or " verHr5.pep").

Sequence ID No. 7 is a nucleotide sequence encoding the novel receptor of the present invention designated as "hXR2".

Sequence ID No. 8 is the amino acid sequence deduced from the nucleotide sequence set forth in Sequence No. 7 (variously referred to herein as receptor "XR2", "hXR2" or "hXR2.pep").

Sequence ID No. 9 is a nucleotide sequence encoding novel receptor of the present invention referred to herein as "mXR4".

Sequence ID No. 10 is the amino acid sequence deduced from the nucleotide sequence of Sequence ID No. 9 (variously referred to herein as receptor "XR4", "mXR4" or "mXR4.pep").

Sequence ID No. 11 is the nucleotide sequence encoding the novel receptor of the present invention referred to as "mXR5".

Sequence ID No. 12 is the amino acid sequence deduced from the nucleotide sequence of Sequence ID No. 11 (variously referred to herein as receptor "XR5", "mXR5" or "mXR5.pep").

Sequence ID No. 13 is the nucleotide sequence encoding the novel receptor of the present invention referred to as "dXR79".

Sequence ID No. 14 is the amino acid sequence deduced from the nucleotide sequence of Sequence ID No. 13 (variously referred to herein as "XR79", "dXR79" or "dXR79.pep").

---

That which is claimed is:

1. A method of testing a compound for its ability to regulate transcription-activating effects of a receptor polypeptide, said method comprising assaying for the presence or absence of reporter protein upon contacting cells containing a receptor polypeptide and reporter vector with said compound;

wherein said receptor polypeptide is characterized by having a DNA binding domain comprising about 66 amino adds with 9 Cys residues, wherein said DNA binding domain is further characterized by the following amino acid sequence identity, relative to the DNA binding domains of hRAR-alpha, hTR-beta, hGR and hRXR-alpha, respectively;

A.
   (i) about 68% amino acid sequence identity with the DNA binding domain of hRAR-alpha;
   (ii) about 59% amino acid sequence identity with the DNA binding domain of the hTR-beta;
   (iii) about 45% amino acid sequence identity with the DNA binding domain of hGR; and
   (iv) about 65% amino acid sequence identity with the DNA binding domain of hRXR-alpha; or B.
   (i) about 55% amino acid sequence identity with the DNA binding domain of hRAR-alpha;
   (ii) about 56% amino acid sequence identity with the DNA binding domain of hTR-beta;
   (iii) about 50% amino acid sequence identity with the DNA binding domain of hGR; and
   (iv) about 52%, amino acid sequence identity with the DNA binding domain of hRXP, alpha; or C.
   (i) about 62% amino acid sequence identity with the DNA binding domain of hRAR-alpha;
   (i) about 58% amino acid sequence identity with the DNA binding domain of hTR-beta;
   (iii) about 48% amino acid sequence identity with the DNA binding domain of hGR; and
   (iv) about 62% amino acid sequence identity with the DNA binding domain of hRXR-alpha; or D.
   (i) about 59% amino acid sequence identity with the DNA binding domain of hRAR-alpha;
   (ii) about 52% amino acid sequence identify with the DNA binding domain of hTR-beta;
   (iii) about 44% amino acid sequence identity with the DNA binding domain of hGR; and
   (iv) about 61% amino acid sequence identity with the DNA binding domain of hRXR-alpha; or E.
   (i) about 59% amino acid sequence identity with the DNA binding domain of hRAR-alpha;
   (ii) about 55% amino acid sequence identity with the DNA binding domain of hTR-beta;
   (iii) about 50% amino acid sequence identity with the DNA binding domain of hGR; and
   (iv) about 65% amino acid sequence identity with the DNA binding domain of hRXR-alpha; and wherein said reporter vector comprises:

(a) a promoter that is operable in said cell,
    a hormone response element, and
(b) a DNA segment encoding a reporter protein,
    wherein said reporter protein-encoding DNA segment is operatively linked to said promoter for transcription of said DNA segment, and
    wherein said hormone response element is operatively linked to said promoter for activation thereof.

2. A method according to claim 1 wherein the ligand binding domain of said receptor polypeptide is characterized by the following amino acid sequence identity, relative to the ligand binding domains of hRAR-alpha, hTR-beta, hGR and hRXR-alpha, respectively:

A.
   (i) about 27% amino acid sequence identity with the ligand binding domain of hRAR-alpha;
   (ii) about 30% amino acid sequence identity with the ligand binding domain of hTR-beta;
   (iii) about 20% amino acid sequence identity with the ligand binding domain of hGR; and
   (iv) about 22% amino acid sequence identity with the ligand binding domain of hRXR-alpha; or B.
   (i) about 32% amino acid sequence identity with the ligand binding domain of hRAR-alpha;
   (ii) about 29% amino acid sequence identity with the ligand binding domain of hTR-beta;
   (iii) about 20% amino acid sequence identity with the ligand binding domain of hGR; and
   (iv) about 23% amino acid sequence identity with the ligand binding domain of hRXR-alpha; or C.
   (i) about 29% amino acid sequence identity with the ligand binding domain of kRAR-alpha;
   (ii) about 27% amino acid sequence identity with the ligand binding domain of hTR-beta;
   (iii) about 21% amino sequence identity with the ligand binding domain of hGR; and
   (iv) about 28% amino acid sequence identity with the ligand binding domain of hRXR-alpha; or D.
   (i) about 19% amino acid sequence identity with the ligand binding domain of hRAR-alpha;
   (ii) about 22% amino acid sequence identity with the ligand binding domain of hTR-beta;
   (iii) about 20% amino acid sequence identity with the ligand binding domain of hGR; and
   (iv) about 27% amino acid sequence identity with the ligand binding domain of hgXR-alpha; or E.
   (i) about 18% amino acid sequence identity with the ligand binding domain of hRAR-alpha;
   (ii) about 20% amino acid sequence identity with the ligand binding domain of hTR-beta;
   (iii) about 20% amino acid sequence identity with the ligand binding domain of hGR; and
   (iv) about 24% amino sequence identity with the ligand binding domain of hRXR-alpha.

3. A method according to claim 2 wherein said receptor polypeptide has an overall amino acid sequence identity, relative to hRAR-alpha, hTR-beta, hGR and hRXR-alpha, respectively of:

A.
- (i) about 32% relative to hgAR-alpha;
- (ii) about 31% relative to hTR-beta;
- (iii) about 18% relative to hGR; and
- (iv) about 29% relative to hRXR-alpha; or B.
- (i) about 33% relative to hRAR-alpha;
- (ii) about 31% relative to hTR-beta;
- (iii) about 24% relative to hGR; and
- (iv) about 27% relative to hRXR-alpha; or C.
- (i) about 32% relative to hRAR-alpha;
- (ii) about 31% relative to hTR-beta;
- (iii) about 25% relative to hGR; and
- (iv) about 33% relative to hRXR-alpha; or D.
- (i) about 27% relative to hRAR-alpha;
- (ii) about 24% relative to hTR-beta;
- (iii) about 20% relative to hGR; and
- (iv) about 29% relative to hRXR-alpha; or E.
- (i) about 24% relative to hRAR-alpha;
- (ii) about 28% relative to hTR-beta;
- (iii) about 18% relative to hGR; and
- (iv) about 33% relative to hRXR-alpha.

4. A method according to claim 3 wherein said receptor polypeptide has the amino acid sequence set forth in SEQ ID NOs:2, 4, 6, 8, 10, 12 or 14.

5. A method according to claim 1 wherein the DNA binding domain of said receptor polypeptide has:
- (i) about 68% amino acid sequence identity with the DNA binding domain of hRAR-alpha;
- (ii) about 59% amino acid sequence identity with the DNA binding domain of hTR-beta;
- (iii) about 45% amino acid sequence identity with the DNA binding domain of hGR; and
- (iv) about 65% amino acid sequence identity with the DNA binding domain of hRAR-alpha.

6. A method according to claim 1 where the DNA binding domain of said receptor polypeptide has;
- (i) about 55% amino acid sequence identity with the DNA binding domain of hKAR-alpha;
- (ii) about 56% amino acid sequence identity with the DNA binding domain of hRAR-beta;
- (iii) about 50% amino acid sequence identity with the DNA binding domain of hGR; and
- (iv) about 52% amino acid sequence identity with the DNA binding domain of hRXR-alpha.

7. A method according to claim 1 wherein the DNA binding domain of said receptor polypeptide has:
- (i) about 62% amino acid sequence identity with the DNA binding domain of hKAR-alpha;
- (ii) about 58% amino acid sequence identity with the DNA binding domain of hTR-beta;
- (iii) about 48% amino acid sequence identity with the DNA binding domain of hGR; and
- (iv) about 62% amino acid sequence identity with the DNA binding domain of hRXR-alpha.

8. A method according to claim 1 wherein the DNA binding domain of said receptor polypeptide has:
- (i) about 59% amino acid sequence identity with the DNA binding domain of hRAR-alpha;
- (ii) about 52% amino acid sequence identity with the DNA binding domain of hTR-beta;
- (iii) about 44% amino acid sequence identity with the DNA binding domain of hGR; and
- (iv) about 61% amino acid sequence identity with the DNA binding domain of hRXR-alpha.

9. A method according to claim 1 wherein the DNA binding domain of said receptor polypeptide has:
- (i) about 59% amino acid sequence identity with the DNA binding domain of hRAR-alpha;
- (ii) about 55% amino acid sequence identity with the DNA binding domain of hTR-beta;
- (iii) about 50% amino acid sequence identity with the DNA binding domain of hGR; and
- (iv) about 65% amino acid sequence identity with the DNA binding domain of hRXR-alpha.

10. A method of testing a compound for its ability to regulate transcription-activating effects of a receptor polypeptide, wherein the ligand binding domain of said receptor polypeptide is characterized by the following amino acid sequence identity, relative to the ligand binding domains of hRAR-alpha, hTR-beta, hGR and hRXR-alpha, respectively:

A.
- (i) about 27% amino acid sequence identity with the ligand binding domain of hRAR-alpha;
- (ii) about 30% amino acid sequence identity with the ligand binding domain of hTR-beta;
- (iii) about 20% amino acid sequence identity with the ligand binding domain of hGR; and
- (iv) about 22% amino acid sequence identity with the ligand binding domain of hRXR-alpha; or B.
- (i) about 32% amino acid sequence identity with the ligand binding domain of hRAR-alpha;
- (ii) about 29% amino acid sequence identity with the ligand binding domain of hTR-beta;
- (iii) about 20% amino acid sequence identity with the ligand binding domain of hGR; and
- (iv) about 23% amino acid sequence identity with the ligand binding domain of hRXR-alpha; or C.
- (i) about 29% amino acid sequence identity with the ligand binding domain of hRAR-alpha:
- (ii) about 27% amino acid sequence identity with the ligand binding domain of hTR-beta;
- (iii) about 21% amino acid sequence identity with the ligand binding domain of hGR; and
- (iv) about 28% amino acid sequence identity with the ligand binding domain of hRXR-alpha; or D.
- (i) about 19% amino acid sequence identity with the ligand binding domain of hRAR-alpha;
- (ii) about 22% amino acid sequence identity with the ligand binding domain of hTR-beta;
- (iii) about 20% amino acid sequence identity with the ligand binding domain of hGIR; and
- (iv) about 27% amino acid sequence identity with the ligand binding domain of hRXR-alpha; or E.
- (i) about 3.8% amino acid sequence identity with the ligand binding domain of hRAR-alpha;
- (ii) about 20% amino acid sequence identity with the ligand binding domain of hTR-beta;
- (iii) about 20% amino acid sequence identity with the ligand binding domain of hGR; and (iv) about 24% amino acid sequence identity with the ligand binding domain of hRXR-alpha, said method comprising:

assaying for the presence or absence of reporter protein upon contacting cells containing a chimeric form of said receptor polypeptide and reporter vector with said compound;

wherein said chimeric form of said receptor polypeptide comprises:

the ligand binding domain of said receptor polypeptide, and the amino-terminal and DNA-binding domains of at least one previously identified member of the steroid/thyroid superfamily of receptors;

wherein said reporter vector comprises:

(a) a promoter that is operable in said cell, (b) a hormone response element which is responsive to the receptor from which the DNA-binding domain of said chimeric form of said receptor polypeptide is derived, and (c) a DNA segment encoding a reporter protein, wherein said reporter protein-encoding DNA segment is operatively linked to said promoter for transcription of said DNA segment, and wherein said hormone response element is operatively linked to said promoter for activation thereof.

11. A method according to claim 10 wherein the ligand binding domain of said receptor polypeptide has:

(i) about 27% amino acid sequence identity with the ligand binding domain of hRAR-alpha;

(ii) about 30% amino acid sequence identity with the ligand binding domain of hTR-beta;

(iii) about 20% amino acid sequence identity with the ligand binding domain of hGR; and (iv) about 22% amino acid sequence identity with the ligand binding domain of hRXR-alpha.

12. A method according to claim 10 wherein the ligand binding domain of said receptor polypeptide has:

(i) about 32% amino acid sequence identity with the ligand binding domain of hRAR-alpha;

(ii) about 29% amino acid sequence identity with the ligand binding domain of hTR-beta;

(iii) about 20% amino acid sequence identity with the ligand binding domain of hGR; and (iv) about 23% amino acid sequence identity with the ligand binding domain of hRXR-alpha.

13. A method according to claim 10 wherein the ligand binding domain of said receptor polypeptide has:

(i) about 29% amino acid sequence identity with the ligand binding domain of hRAR-alpha;

(ii) about 27% amino acid sequence identity with the ligand binding domain of hTR-beta;

(iii) about 21% amino acid sequence identity with the ligand binding domain of hGR; and (iv) about 28% amino acid sequence identity with the ligand binding domain of hRXR-alpha.

14. A method according to claim 10 wherein the ligand binding domain of said receptor polypeptide has:

(i) about 19% amino acid sequence identity with the ligand binding domain of hRAR-alpha;

(ii) about 22% amino acid sequence identity with the ligand binding domain of hTR-beta;

(iii) about 20% amino acid sequence identity with the ligand binding domain of hGR; and (iv) about 27% amino acid sequence identity with the ligand binding domain of hRXR-alpha.

15. A method according to claim 10 wherein the ligand binding domain of said receptor polypeptide has:

(i) about 18% amino acid sequence identity with the ligand binding domain of hRAR-alpha;

(ii) about 20% amino acid sequence identity with the ligand binding domain of hTR-beta;

(iii) about 20% amino acid sequence identity with the ligand binding domain of hGR; and (iv) about 24% amino acid sequence identity with the ligand binding domain of hRXR-alpha.

16. A method according to claim 10 wherein said at least one previously identified member of the steroid/thyroid superfamily of receptors is selected from glucocorticoid receptor (GR), thyroid receptors (TR), retinoic acid receptors (RAR), mineraloeorticoid receptor (MR), estrogen receptor (ER), estrogen related receptor, retinoid X receptor, vitamin D receptor (VDR), aldosterone receptor (AR), progesterone receptor (PR), ultraspiracle receptor (USP), nerve growth factor induced protein-B (NGFI-B), the coup family of transcription factors (COUP), peroxisome proliferatar-activated receptor (PPAR), or mammalian receptor TR2 (TR2).

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1952 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR1 (VERHT19.SEQ)

( i x ) FEATURE:
        ( A ) NAME/KEY: CDS
        ( B ) LOCATION: 79..1725

( i x ) FEATURE:
        ( A ) NAME/KEY: misc_feature
        ( B ) LOCATION: 349..1952
        ( D ) OTHER INFORMATION: /product="Carboxy terminal portion of XR1 variant verht3"

( i x ) FEATURE:
        ( A ) NAME/KEY: misc_feature
        ( B ) LOCATION: 352..1952
        ( D ) OTHER INFORMATION: /product="Carboxy terminal portion of XR1 variant verhr5"

( x i ) SEQUENCE DESCRIPTION: SEQ ID NO:1:

```
GAATTCGGGG ACTCCATAGT ACACTGGGGC AAAGCACAGC CCCAGTTTCT GGAGGCAGAT        60

GGGTAACCAG GAAAAGGC ATG AAT GAG GGG GCC CCA GGA GAC AGT GAC TTA        111
                    Met Asn Glu Gly Ala Pro Gly Asp Ser Asp Leu
                     1               5                  10

GAG ACT GAG GCA AGA GTG CCG TGG TCA ATC ATG GGT CAT TGT CTT CGA        159
```

-continued

| | | | | | | | | | | | | | | | | |
|---|---|---|---|---|---|---|---|---|---|---|---|---|---|---|---|---|
| Glu | Thr | Glu | Ala 15 | Arg | Val | Pro | Trp | Ser 20 | Ile | Met | Gly | His | Cys 25 | Leu | Arg | |
| ACT Thr | GGA Gly | CAG Gln 30 | GCC Ala | AGA Arg | ATG Met | TCT Ser | GCC Ala | ACA Thr 35 | CCC Pro | ACA Thr | CCT Pro | GCA Ala | GGT Gly 40 | GAA Glu | GGA Gly | 207 |
| GCC Ala | AGA Arg 45 | AGC Ser | TCT Ser | TCA Ser | ACC Thr | TGT Cys 50 | AGC Ser | TCC Ser | CTG Leu | AGC Ser | AGG Arg 55 | CTG Leu | TTC Phe | TGG Trp | TCT Ser | 255 |
| CAA Gln 60 | CTT Leu | GAG Glu | CAC His | ATA Ile | AAC Asn 65 | TGG Trp | GAT Asp | GGA Gly | GCC Ala | ACA Thr 70 | GCC Ala | AAG Lys | AAC Asn | TTT Phe | ATT Ile 75 | 303 |
| AAT Asn | TTA Leu | AGG Arg | GAG Glu | TTC Phe 80 | TTC Phe | TCT Ser | TTT Phe | CTC Leu | CTC Leu 85 | CCT Pro | GCA Ala | TTG Leu | AGA Arg | AAA Lys 90 | GCT Ala | 351 |
| CAA Gln | ATT Ile | GAA Glu | ATT Ile 95 | ATT Ile | CCA Pro | TGC Cys | AAG Lys | ATC Ile 100 | TGT Cys | GGA Gly | GAC Asp | AAA Lys | TCA Ser 105 | TCA Ser | GGA Gly | 399 |
| ATC Ile | CAT His | TAT Tyr 110 | GGT Gly | GTC Val | ATT Ile | ACA Thr | TGT Cys 115 | GAA Glu | GGC Gly | TGC Cys | AAG Lys | GGC Gly 120 | TTT Phe | TTC Phe | AGG Arg | 447 |
| AGA Arg | AGT Ser 125 | CAG Gln | CAA Gln | AGC Ser | AAT Asn | GCC Ala 130 | ACC Thr | TAC Tyr | TCC Ser | TGT Cys | CCT Pro 135 | CGT Arg | CAG Gln | AAG Lys | AAC Asn | 495 |
| TGT Cys 140 | TTG Leu | ATT Ile | GAT Asp | CGA Arg | ACC Thr 145 | AGT Ser | AGA Arg | AAC Asn | CGC Arg | TGC Cys 150 | CAA Gln | CAC His | TGT Cys | CGA Arg | TTA Leu 155 | 543 |
| CAG Gln | AAA Lys | TGC Cys | CTT Leu | GCC Ala 160 | GTA Val | GGG Gly | ATG Met | TCT Ser | CGA Arg 165 | GAT Asp | GCT Ala | GTA Val | AAA Lys | TTT Phe 170 | GGC Gly | 591 |
| CGA Arg | ATG Met | TCA Ser 175 | AAA Lys | AAG Lys | CAG Gln | AGA Arg | GAC Asp 180 | AGC Ser | TTG Leu | TAT Tyr | GCA Ala | GAA Glu 185 | GTA Val | CAG Gln | AAA Lys | 639 |
| CAC His | CGG Arg | ATG Met 190 | CAG Gln | CAG Gln | CAG Gln | CAG Gln | CGC Arg 195 | GAC Asp | CAC His | CAG Gln | CAG Gln | CAG Gln 200 | CCT Pro | GGA Gly | GAG Glu | 687 |
| GCT Ala | GAG Glu 205 | CCG Pro | CTG Leu | ACG Thr | CCC Pro | ACC Thr 210 | TAC Tyr | AAC Asn | ATC Ile | TCG Ser | GCC Ala 215 | AAC Asn | GGG Gly | CTG Leu | ACG Thr | 735 |
| GAA Glu 220 | CTT Leu | CAC His | GAC Asp | GAC Asp | CTC Leu 225 | AGT Ser | AAC Asn | TAC Tyr | ATT Ile | GAC Asp 230 | GGG Gly | CAC His | ACC Thr | CCT Pro | GAG Glu 235 | 783 |
| GGG Gly | AGT Ser | AAG Lys | GCA Ala | GAC Asp 240 | TCC Ser | GCC Ala | GTC Val | AGC Ser | AGC Ser 245 | TTC Phe | TAC Tyr | CTG Leu | GAC Asp | ATA Ile 250 | CAG Gln | 831 |
| CCT Pro | TCC Ser | CCA Pro | GAC Asp 255 | CAG Gln | TCA Ser | GGT Gly | CTT Leu | GAT Asp 260 | ATC Ile | AAT Asn | GGA Gly | ATC Ile | AAA Lys 265 | CCA Pro | GAA Glu | 879 |
| CCA Pro | ATA Ile | TGT Cys 270 | GAC Asp | TAC Tyr | ACA Thr | CCA Pro | GCA Ala 275 | TCA Ser | GGC Gly | TTC Phe | TTT Phe | CCC Pro 280 | TAC Tyr | TGT Cys | TCG Ser | 927 |
| TTC Phe | ACC Thr 285 | AAC Asn | GGC Gly | GAG Glu | ACT Thr | TCC Ser 290 | CCA Pro | ACT Thr | GTG Val | TCC Ser | ATG Met 295 | GCA Ala | GAA Glu | TTA Leu | GAA Glu | 975 |
| CAC His 300 | CTT Leu | GCA Ala | CAG Gln | AAT Asn | ATA Ile 305 | TCT Ser | AAA Lys | TCG Ser | CAT His | CTG Leu 310 | GAA Glu | ACC Thr | TGC Cys | CAA Gln | TAC Tyr 315 | 1023 |
| TTG Leu | AGA Arg | GAA Glu | GAG Glu | CTC Leu 320 | CAG Gln | CAG Gln | ATA Ile | ACG Thr | TGG Trp 325 | CAG Gln | ACC Thr | TTT Phe | TTA Leu | CAG Gln 330 | GAA Glu | 1071 |
| GAA Glu | ATT Ile | GAG Glu | AAC Asn | TAT Tyr | CAA Gln | AAC Asn | AAG Lys | CAG Gln | CGG Arg | GAG Glu | GTG Val | ATG Met | TGG Trp | CAA Gln | TTG Leu | 1119 |

-continued

| | | | | | | | | | | | | | | |
|---|---|---|---|---|---|---|---|---|---|---|---|---|---|---|
|Glu|Ile|Glu|Asn|Tyr|Gln|Asn|Lys|Gln|Arg|Glu|Val|Met|Trp|Gln|Leu|
| | |335| | | |340| | | | |345| | | |

```
TGT GCC ATC AAA ATT ACA GAA GCT ATA CAG TAT GTG GTG GAG TTT GCC      1167
Cys Ala Ile Lys Ile Thr Glu Ala Ile Gln Tyr Val Val Glu Phe Ala
        350                 355                 360

AAA CGC ATT GAT GGA TTT ATG GAA CTG TGT CAA AAT GAT CAA ATT GTG      1215
Lys Arg Ile Asp Gly Phe Met Glu Leu Cys Gln Asn Asp Gln Ile Val
    365                 370                 375

CTT CTA AAA GCA GGT TCT CTA GAG GTG GTG TTT ATC AGA ATG TGC CGT      1263
Leu Leu Lys Ala Gly Ser Leu Glu Val Val Phe Ile Arg Met Cys Arg
380                 385                 390                 395

GCC TTT GAC TCT CAG AAC AAC ACC GTG TAC TTT GAT GGG AAG TAT GCC      1311
Ala Phe Asp Ser Gln Asn Asn Thr Val Tyr Phe Asp Gly Lys Tyr Ala
                400                 405                 410

AGC CCC GAC GTC TTC AAA TCC TTA GGT TGT GAA GAC TTT ATT AGC TTT      1359
Ser Pro Asp Val Phe Lys Ser Leu Gly Cys Glu Asp Phe Ile Ser Phe
            415                 420                 425

GTG TTT GAA TTT GGA AAG AGT TTA TGT TCT ATG CAC CTG ACT GAA GAT      1407
Val Phe Glu Phe Gly Lys Ser Leu Cys Ser Met His Leu Thr Glu Asp
        430                 435                 440

GAA ATT GCA TTA TTT TCT GCA TTT GTA CTG ATG TCA GCA GAT CGC TCA      1455
Glu Ile Ala Leu Phe Ser Ala Phe Val Leu Met Ser Ala Asp Arg Ser
    445                 450                 455

TGG CTG CAA GAA AAG GTA AAA ATT GAA AAA CTG CAA CAG AAA ATT CAG      1503
Trp Leu Gln Glu Lys Val Lys Ile Glu Lys Leu Gln Gln Lys Ile Gln
460                 465                 470                 475

CTA GCT CTT CAA CAC GTC CTA CAG AAG AAT CAC CGA GAA GAT GGA ATA      1551
Leu Ala Leu Gln His Val Leu Gln Lys Asn His Arg Glu Asp Gly Ile
                480                 485                 490

CTA ACA AAG TTA ATA TGC AAG GTG TCT ACA TTA AGA GCC TTA TGT GGA      1599
Leu Thr Lys Leu Ile Cys Lys Val Ser Thr Leu Arg Ala Leu Cys Gly
            495                 500                 505

CGA CAT ACA GAA AAG CTA ATG GCA TTT AAA GCA ATA TAC CCA GAC ATT      1647
Arg His Thr Glu Lys Leu Met Ala Phe Lys Ala Ile Tyr Pro Asp Ile
        510                 515                 520

GTG CGA CTT CAT TTT CCT CCA TTA TAC AAG GAG TTG TTC ACT TCA GAA      1695
Val Arg Leu His Phe Pro Pro Leu Tyr Lys Glu Leu Phe Thr Ser Glu
    525                 530                 535

TTT GAG CCA GCA ATG CAA ATT GAT GGG     TAAATGTTAT CACCTAAGCA        1742
Phe Glu Pro Ala Met Gln Ile Asp Gly
540                 545

CTTCTAGAAT GTCTGAAGTA CAAACATGAA AAACAAACAA AAAAATTAAC CGAGACACTT   1802

TATATGGCCC TGCACAGACC TGGAGCGCCA CACACTGCAC ATCTTTGGT GATCGGGGTC    1862

AGGCAAAGGA GGGGAAACAA TGAAAACAAA TAAAGTTGAA CTTGTTTTTC TCAAAAAAAA   1922

AAAAAAAAAA AAAAAAAAA AAAAAAAAA                                      1952
```

( 2 ) INFORMATION FOR SEQ ID NO:2:

( i ) SEQUENCE CHARACTERISTICS:
        ( A ) LENGTH: 548 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Glu Gly Ala Pro Gly Asp Ser Asp Leu Glu Thr Glu Ala Arg
 1               5                  10                  15

Val Pro Trp Ser Ile Met Gly His Cys Leu Arg Thr Gly Gln Ala Arg
            20                  25                  30
```

```
Met  Ser  Ala  Thr  Pro  Thr  Pro  Ala  Gly  Glu  Gly  Ala  Arg  Ser  Ser  Ser
          35                  40                      45

Thr  Cys  Ser  Ser  Leu  Ser  Arg  Leu  Phe  Trp  Ser  Gln  Leu  Glu  His  Ile
     50                       55                  60

Asn  Trp  Asp  Gly  Ala  Thr  Ala  Lys  Asn  Phe  Ile  Asn  Leu  Arg  Glu  Phe
65                       70                  75                            80

Phe  Ser  Phe  Leu  Leu  Pro  Ala  Leu  Arg  Lys  Ala  Gln  Ile  Glu  Ile  Ile
                    85                  90                            95

Pro  Cys  Lys  Ile  Cys  Gly  Asp  Lys  Ser  Ser  Gly  Ile  His  Tyr  Gly  Val
               100                      105                      110

Ile  Thr  Cys  Glu  Gly  Cys  Lys  Gly  Phe  Phe  Arg  Arg  Ser  Gln  Gln  Ser
          115                      120                      125

Asn  Ala  Thr  Tyr  Ser  Cys  Pro  Arg  Gln  Lys  Asn  Cys  Leu  Ile  Asp  Arg
     130                      135                      140

Thr  Ser  Arg  Asn  Arg  Cys  Gln  His  Cys  Arg  Leu  Gln  Lys  Cys  Leu  Ala
145                           150                      155                      160

Val  Gly  Met  Ser  Arg  Asp  Ala  Val  Lys  Phe  Gly  Arg  Met  Ser  Lys  Lys
                    165                      170                      175

Gln  Arg  Asp  Ser  Leu  Tyr  Ala  Glu  Val  Gln  Lys  His  Arg  Met  Gln  Gln
               180                      185                      190

Gln  Gln  Arg  Asp  His  Gln  Gln  Pro  Gly  Glu  Ala  Glu  Pro  Leu  Thr
          195                      200                      205

Pro  Thr  Tyr  Asn  Ile  Ser  Ala  Asn  Gly  Leu  Thr  Glu  Leu  His  Asp  Asp
     210                      215                      220

Leu  Ser  Asn  Tyr  Ile  Asp  Gly  His  Thr  Pro  Glu  Gly  Ser  Lys  Ala  Asp
225                           230                      235                      240

Ser  Ala  Val  Ser  Ser  Phe  Tyr  Leu  Asp  Ile  Gln  Pro  Ser  Pro  Asp  Gln
                    245                      250                      255

Ser  Gly  Leu  Asp  Ile  Asn  Gly  Ile  Lys  Pro  Glu  Pro  Ile  Cys  Asp  Tyr
               260                      265                      270

Thr  Pro  Ala  Ser  Gly  Phe  Phe  Pro  Tyr  Cys  Ser  Phe  Thr  Asn  Gly  Glu
          275                      280                      285

Thr  Ser  Pro  Thr  Val  Ser  Met  Ala  Glu  Leu  Glu  His  Leu  Ala  Gln  Asn
     290                      295                      300

Ile  Ser  Lys  Ser  His  Leu  Glu  Thr  Cys  Gln  Tyr  Leu  Arg  Glu  Glu  Leu
305                           310                      315                      320

Gln  Gln  Ile  Thr  Trp  Gln  Thr  Phe  Leu  Gln  Glu  Glu  Ile  Glu  Asn  Tyr
                    325                      330                      335

Gln  Asn  Lys  Gln  Arg  Glu  Val  Met  Trp  Gln  Leu  Cys  Ala  Ile  Lys  Ile
               340                      345                      350

Thr  Glu  Ala  Ile  Gln  Tyr  Val  Val  Glu  Phe  Ala  Lys  Arg  Ile  Asp  Gly
          355                      360                      365

Phe  Met  Glu  Leu  Cys  Gln  Asn  Asp  Gln  Ile  Val  Leu  Leu  Lys  Ala  Gly
     370                      375                      380

Ser  Leu  Glu  Val  Val  Phe  Ile  Arg  Met  Cys  Arg  Ala  Phe  Asp  Ser  Gln
385                           390                      395                      400

Asn  Asn  Thr  Val  Tyr  Phe  Asp  Gly  Lys  Tyr  Ala  Ser  Pro  Asp  Val  Phe
                    405                      410                      415

Lys  Ser  Leu  Gly  Cys  Glu  Asp  Phe  Ile  Ser  Phe  Val  Phe  Glu  Phe  Gly
               420                      425                      430

Lys  Ser  Leu  Cys  Ser  Met  His  Leu  Thr  Glu  Asp  Glu  Ile  Ala  Leu  Phe
          435                      440                      445

Ser  Ala  Phe  Val  Leu  Met  Ser  Ala  Asp  Arg  Ser  Trp  Leu  Gln  Glu  Lys
```

```
            450                    455                        460
Val Lys Ile Glu Lys Leu Gln Gln Lys Ile Gln Leu Ala Leu Gln His
465                     470                    475                    480
Val Leu Gln Lys Asn His Arg Glu Asp Gly Ile Leu Thr Lys Leu Ile
                    485                    490                    495
Cys Lys Val Ser Thr Leu Arg Ala Leu Cys Gly Arg His Thr Glu Lys
                500                    505                    510
Leu Met Ala Phe Lys Ala Ile Tyr Pro Asp Ile Val Arg Leu His Phe
                515                    520                    525
Pro Pro Leu Tyr Lys Glu Leu Phe Thr Ser Glu Phe Glu Pro Ala Met
                530                    535                540
Gln Ile Asp Gly
545
```

( 2 ) INFORMATION FOR SEQ ID NO:3:

( i ) SEQUENCE CHARACTERISTICS:
      ( A ) LENGTH: 386 base pairs
      ( B ) TYPE: nucleic acid
      ( C ) STRANDEDNESS: single
      ( D ) TOPOLOGY: linear ( i i ) MOLECULE TYPE: cDNA ( v i i ) IMMEDIATE SOURCE:
      ( B ) CLONE: AMINO TERMINAL PORTION OF XR1PRIME
         ( VERHT3 . SEQ )

( i x ) FEATURE:
      ( A ) NAME/KEY: CDS
      ( B ) LOCATION: 90..386

( x i ) SEQUENCE DESCRIPTION: SEQ ID NO:3:

```
CCATCTGTCT  DATCACCTTG  GACTCCATAG  TACACTGGGG  CAAAGCACAG  CCCCAGTTTC                60

TGGAGGCAGA  TGGGTAACCA  GGAAAAGGC  ATG AAT GAG GGG GCC CCA GGA GAC                   113
                                   Met Asn Glu Gly Ala Pro Gly Asp
                                    1               5

AGT GAC TTA GAG ACT GAG GCA AGA GTG CCG TGG TCA ATC ATG GGT CAT                      161
Ser Asp Leu Glu Thr Glu Ala Arg Val Pro Trp Ser Ile Met Gly His
         10                  15                  20

TGT CTT CGA ACT GGA CAG GCC AGA ATG TCT GCC ACA CCC ACA CCT GCA                      209
Cys Leu Arg Thr Gly Gln Ala Arg Met Ser Ala Thr Pro Thr Pro Ala
 25                  30                  35                  40

GGT GAA GGA GCC AGA AGG GAT GAA CTT TTT GGG ATT CTC CAA ATA CTC                      257
Gly Glu Gly Ala Arg Arg Asp Glu Leu Phe Gly Ile Leu Gln Ile Leu
                 45                  50                  55

CAT CAG TGT ATC CTG TCT TCA GGT GAT GCT TTT GTT CTT ACT GGC GTC                      305
His Gln Cys Ile Leu Ser Ser Gly Asp Ala Phe Val Leu Thr Gly Val
             60                  65                  70

TGT TGT TCC TGG AGG CAG AAT GGC AAG CCA CCA TAT TCA CAA AAG GAA                      353
Cys Cys Ser Trp Arg Gln Asn Gly Lys Pro Pro Tyr Ser Gln Lys Glu
         75                  80                  85

GAT AAG GAA GTA CAA ACT GGA TAC ATG AAT GCT                                          386
Asp Lys Glu Val Gln Thr Gly Tyr Met Asn Ala
         90                  95
```

( 2 ) INFORMATION FOR SEQ ID NO:4:

( i ) SEQUENCE CHARACTERISTICS:
      ( A ) LENGTH: 99 amino acids
      ( B ) TYPE: amino acid
      ( D ) TOPOLOGY: linear ( i i ) MOLECULE TYPE: protein ( x i ) SEQUENCE DESCRIPTION: SEQ ID NO:4:

| Met | Asn | Glu | Gly | Ala | Pro | Gly | Asp | Ser | Asp | Leu | Glu | Thr | Glu | Ala | Arg |
| 1 | | | | 5 | | | | | 10 | | | | | 15 | |

| Val | Pro | Trp | Ser | Ile | Met | Gly | His | Cys | Leu | Arg | Thr | Gly | Gln | Ala | Arg |
| | | | 20 | | | | | 25 | | | | | 30 | | |

| Met | Ser | Ala | Thr | Pro | Thr | Pro | Ala | Gly | Glu | Gly | Ala | Arg | Arg | Asp | Glu |
| | | | 35 | | | | 40 | | | | | 45 | | | |

| Leu | Phe | Gly | Ile | Leu | Gln | Ile | Leu | His | Gln | Cys | Ile | Leu | Ser | Ser | Gly |
| | | 50 | | | | | 55 | | | | | 60 | | | |

| Asp | Ala | Phe | Val | Leu | Thr | Gly | Val | Cys | Cys | Ser | Trp | Arg | Gln | Asn | Gly |
| 65 | | | | | 70 | | | | | 75 | | | | | 80 |

| Lys | Pro | Pro | Tyr | Ser | Gln | Lys | Glu | Asp | Lys | Glu | Val | Gln | Thr | Gly | Tyr |
| | | | | 85 | | | | | 90 | | | | | 95 | |

| Met | Asn | Ala |
| | | |

( 2 ) INFORMATION FOR SEQ ID NO:5:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: AMINO TERMINAL PORTION OF XR1PRIM2
        ( VERHT5 . SEQ )

( i x ) FEATURE:
        ( A ) NAME/KEY: CDS
        ( B ) LOCATION: 103..300

( x i ) SEQUENCE DESCRIPTION: SEQ ID NO:5:

```
GTTTTTTTTT TTTTTTGGT ACCATAGAGT TGCTCTGAAA ACAGAAGATA GAGGGAGTCT        60

CGGAGCTCGC CATCTCCAGC GATCTCTACA TTGGGAAAAA AC ATG GAG TCA GCT       114
                                                 Met Glu Ser Ala
                                                   1
```

| CCG | GCA | AGG | GAG | ACC | CCG | CTG | AAC | CAG | GAA | TCC | GCC | GCC | CCC | GAC | CCC | 162 |
| Pro | Ala | Arg | Glu | Thr | Pro | Leu | Asn | Gln | Glu | Ser | Ala | Ala | Pro | Asp | Pro | |
| 5 | | | | 10 | | | | | 15 | | | | | 20 | | |

| GCC | GCC | AGC | GAG | CCA | GGC | AGC | AGC | GGC | GCG | GAC | GCG | GCC | GCC | GGC | TCC | 210 |
| Ala | Ala | Ser | Glu | Pro | Gly | Ser | Ser | Gly | Ala | Asp | Ala | Ala | Ala | Gly | Ser | |
| | | 25 | | | | | 30 | | | | | 35 | | | | |

| CGC | AAG | AGC | GAG | CCG | CCT | GCC | CCG | GTG | CGC | AGA | CAG | AGC | TAT | TCC | AGC | 258 |
| Arg | Lys | Ser | Glu | Pro | Pro | Ala | Pro | Val | Arg | Arg | Gln | Ser | Tyr | Ser | Ser | |
| | | | 40 | | | | | 45 | | | | | 50 | | | |

| ACC | AGC | AGA | GGT | ATC | TCA | GTA | ACG | AAG | AAG | ACA | CAT | ACA | TCT | | | 300 |
| Thr | Ser | Arg | Gly | Ile | Ser | Val | Thr | Lys | Lys | Thr | His | Thr | Ser | | | |
| | | 55 | | | | | 60 | | | | | 65 | | | | |

( 2 ) INFORMATION FOR SEQ ID NO:6:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Glu | Ser | Ala | Pro | Ala | Arg | Glu | Thr | Pro | Leu | Asn | Gln | Glu | Ser | Ala |
| 1 | | | | 5 | | | | | 10 | | | | | 15 | |

```
Ala Pro Asp Pro Ala Ala Ser Glu Pro Gly Ser Ser Gly Ala Asp Ala
         20                  25                  30

Ala Ala Gly Ser Arg Lys Ser Glu Pro Pro Ala Pro Val Arg Arg Gln
         35                  40                  45

Ser Tyr Ser Ser Thr Ser Arg Gly Ile Ser Val Thr Lys Lys Thr His
     50                  55                  60

Thr Ser
 65
```

( 2 ) INFORMATION FOR SEQ ID NO:7:

( i ) SEQUENCE CHARACTERISTICS:
        ( A ) LENGTH: 1659 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR2 (XR2.SEG)

( i x ) FEATURE:
        ( A ) NAME/KEY: CDS
        ( B ) LOCATION: 148..1470

( x i ) SEQUENCE DESCRIPTION: SEQ ID NO:7:

```
GATATCCGTG ACATCATTGC CTGAGTCCAC TGCAAAAAGC TGTCCCCAGA GCAGGAGGGC        60

AATGACAGCT CCCAGGGCAC TCATCTTGAC TGCTCTTGCC TGGGGATTTG GACAGTGCCT       120

TGGTAATGAC CAGGGCTCCA GAAAGAG ATG TCC TTG TGG CTG GGG GCC CCT           171
                              Met Ser Leu Trp Leu Gly Ala Pro
                                1               5

GTG CCT GAC ATT CCT CCT GAC TCT GCG GTG GAG CTG TGG AAG CCA GGC         219
Val Pro Asp Ile Pro Pro Asp Ser Ala Val Glu Leu Trp Lys Pro Gly
         10                  15                  20

GCA CAG GAT GCA AGC AGC CAG GCC CAG GGA GGC AGC AGC TGC ATC CTC         267
Ala Gln Asp Ala Ser Ser Gln Ala Gln Gly Gly Ser Ser Cys Ile Leu
 25                  30                  35                  40

AGA GAG GAA GCC AGG ATG CCC CAC TCT GCT GGG GGT ACT GCA GAG CCC         315
Arg Glu Glu Ala Arg Met Pro His Ser Ala Gly Gly Thr Ala Glu Pro
                 45                  50                  55

ACA GCC CTG CTC ACC AGG GCA GAG CCC CCT TCA GAA CCC ACA GAG ATC         363
Thr Ala Leu Leu Thr Arg Ala Glu Pro Pro Ser Glu Pro Thr Glu Ile
             60                  65                  70

CGT CCA CAA AAG CGG AAA AAG GGG CCA GCC CCC AAA ATG CTG GGG AAC         411
Arg Pro Gln Lys Arg Lys Lys Gly Pro Ala Pro Lys Met Leu Gly Asn
         75                  80                  85

GAG CTA TGC AGC GTG TGT GGG GAC AAG GCC TCG GGC TTC CAC TAC AAT         459
Glu Leu Cys Ser Val Cys Gly Asp Lys Ala Ser Gly Phe His Tyr Asn
     90                  95                 100

GTT CTG AGC TGC GAG GGC TGC AAG GGA TTC TTC CGC CGC AGC GTC ATC         507
Val Leu Ser Cys Glu Gly Cys Lys Gly Phe Phe Arg Arg Ser Val Ile
105                 110                 115                 120

AAG GGA GCG CAC TAC ATC TGC CAC AGT GGC GGC CAC TGC CCC ATG GAC         555
Lys Gly Ala His Tyr Ile Cys His Ser Gly Gly His Cys Pro Met Asp
                125                 130                 135

ACC TAC ATG CGT CGC AAG TGC CAG GAG TGT CGG CTT CGC AAA TGC CGT         603
Thr Tyr Met Arg Arg Lys Cys Gln Glu Cys Arg Leu Arg Lys Cys Arg
            140                 145                 150

CAG GCT GGC ATG CGG GAG GAG TGT GTC CTG TCA GAA GAA CAG ATC CGC         651
Gln Ala Gly Met Arg Glu Glu Cys Val Leu Ser Glu Glu Gln Ile Arg
        155                 160                 165
```

```
CTG AAG AAA CTG AAG CGG CAA GAG GAG GAA CAG GCT CAT GCC ACA TCC    699
Leu Lys Lys Leu Lys Arg Gln Glu Glu Glu Gln Ala His Ala Thr Ser
    170             175                 180

TTG CCC CCC AGG CGT TCC TCA CCC CCC CAA ATC CTG CCC CAG CTC AGC    747
Leu Pro Pro Arg Arg Ser Ser Pro Pro Gln Ile Leu Pro Gln Leu Ser
185             190                 195                 200

CCG GAA CAA CTG GGC ATG ATC GAG AAG CTC GTC GCT GCC CAG CAA CAG    795
Pro Glu Gln Leu Gly Met Ile Glu Lys Leu Val Ala Ala Gln Gln Gln
                205                 210                 215

TGT AAC CGG CGC TCC TTT TCT GAC CGG CTT CGA GTC ACG CCT TGG CCC    843
Cys Asn Arg Arg Ser Phe Ser Asp Arg Leu Arg Val Thr Pro Trp Pro
            220                 225                 230

ATG GCA CCA GAT CCC CAT AGC CGG GAG GCC CGT CAG CAG CGC TTT GCC    891
Met Ala Pro Asp Pro His Ser Arg Glu Ala Arg Gln Gln Arg Phe Ala
        235                 240                 245

CAC TTC ACT GAG CTG GCC ATC GTC TCT GTG CAG GAG ATA GTT GAC TTT    939
His Phe Thr Glu Leu Ala Ile Val Ser Val Gln Glu Ile Val Asp Phe
    250                 255                 260

GCT AAA CAG CTA CCC GGC TTC CTG CAG CTC AGC CGG GAG GAC CAG ATT    987
Ala Lys Gln Leu Pro Gly Phe Leu Gln Leu Ser Arg Glu Asp Gln Ile
265             270                 275                 280

GCC CTG CTG AAG ACC TCT GCG ATC GAG GTG ATG CTT CTG GAG ACA TCT   1035
Ala Leu Leu Lys Thr Ser Ala Ile Glu Val Met Leu Leu Glu Thr Ser
                285                 290                 295

CGG AGG TAC AAC CCT GGG AGT GAG AGT ATC ACC TTC CTC AAG GAT TTC   1083
Arg Arg Tyr Asn Pro Gly Ser Glu Ser Ile Thr Phe Leu Lys Asp Phe
            300                 305                 310

AGT TAT AAC CGG GAA GAC TTT GCC AAA GCA GGG CTG CAA GTG GAA TTC   1131
Ser Tyr Asn Arg Glu Asp Phe Ala Lys Ala Gly Leu Gln Val Glu Phe
        315                 320                 325

ATC AAC CCC ATC TTC GAG TTC TCC AGG GCC ATG AAT GAG CTG CAA CTC   1179
Ile Asn Pro Ile Phe Glu Phe Ser Arg Ala Met Asn Glu Leu Gln Leu
    330                 335                 340

AAT GAT GCC GAG TTT GCC TTG CTC ATT GCT ATC AGC ATC TTC TCT GCA   1227
Asn Asp Ala Glu Phe Ala Leu Leu Ile Ala Ile Ser Ile Phe Ser Ala
345             350                 355                 360

GAC CGG CCC AAC GTG CAG GAC CAG CTC CAG GTG GAG AGG CTG CAG CAC   1275
Asp Arg Pro Asn Val Gln Asp Gln Leu Gln Val Glu Arg Leu Gln His
                365                 370                 375

ACA TAT GTG GAA GCC CTG CAT GCC TAC GTC TCC ATC CAC CAT CCC CAT   1323
Thr Tyr Val Glu Ala Leu His Ala Tyr Val Ser Ile His His Pro His
            380                 385                 390

GAC CGA CTG ATG TTC CCA CGG ATG CTA ATG AAA CTG GTG AGC CTC CGG   1371
Asp Arg Leu Met Phe Pro Arg Met Leu Met Lys Leu Val Ser Leu Arg
        395                 400                 405

ACC CTG AGC AGC GTC CAC TCA GAG CAA GTG TTT GCA CTG CGT CTG CAG   1419
Thr Leu Ser Ser Val His Ser Glu Gln Val Phe Ala Leu Arg Leu Gln
    410                 415                 420

GAC AAA AAG CTC CCA CCG CTG CTC TCT GAG ATC TGG GAT GTG CAC GAA   1467
Asp Lys Lys Leu Pro Pro Leu Leu Ser Glu Ile Trp Asp Val His Glu
425             430                 435                 440

TGACTGTTCT GTCCCCATAT TTTCTGTTTT CTTGGCCGGA TGGCTGAGGC CTGGTGGCTG   1527

CCTCCTAGAA GTGGAACAGA CTGAGAAGGG CAAACATTCC TGGGAGCTGG GCAAGGAGAT   1587

CCTCCCGTGG CATTAAAAGA GAGTCAAAGG GTAAAAAAAA AAAAAAAAAA AAAAAAAAA    1647

AAAAAGGAAT TC                                                      1659
```

( 2 ) INFORMATION FOR SEQ ID NO:8:

( i ) SEQUENCE CHARACTERISTICS:
    ( A ) LENGTH: 440 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Met Ser Leu Trp Leu Gly Ala Pro Val Pro Asp Ile Pro Pro Asp Ser
 1               5                  10                  15
Ala Val Glu Leu Trp Lys Pro Gly Ala Gln Asp Ala Ser Ser Gln Ala
                20                  25                  30
Gln Gly Gly Ser Ser Cys Ile Leu Arg Glu Glu Ala Arg Met Pro His
            35                  40                  45
Ser Ala Gly Gly Thr Ala Glu Pro Thr Ala Leu Leu Thr Arg Ala Glu
        50                  55                  60
Pro Pro Ser Glu Pro Thr Glu Ile Arg Pro Gln Lys Arg Lys Lys Gly
65                  70                  75                  80
Pro Ala Pro Lys Met Leu Gly Asn Glu Leu Cys Ser Val Cys Gly Asp
                85                  90                  95
Lys Ala Ser Gly Phe His Tyr Asn Val Leu Ser Cys Glu Gly Cys Lys
            100                 105                 110
Gly Phe Phe Arg Arg Ser Val Ile Lys Gly Ala His Tyr Ile Cys His
        115                 120                 125
Ser Gly His Cys Pro Met Asp Thr Tyr Met Arg Arg Lys Cys Gln
    130                 135                 140
Glu Cys Arg Leu Arg Lys Cys Arg Gln Ala Gly Met Arg Glu Glu Cys
145                 150                 155                 160
Val Leu Ser Glu Glu Gln Ile Arg Leu Lys Lys Leu Lys Arg Gln Glu
                165                 170                 175
Glu Glu Gln Ala His Ala Thr Ser Leu Pro Pro Arg Arg Ser Ser Pro
            180                 185                 190
Pro Gln Ile Leu Pro Gln Leu Ser Pro Glu Gln Leu Gly Met Ile Glu
        195                 200                 205
Lys Leu Val Ala Ala Gln Gln Gln Cys Asn Arg Arg Ser Phe Ser Asp
    210                 215                 220
Arg Leu Arg Val Thr Pro Trp Pro Met Ala Pro Asp Pro His Ser Arg
225                 230                 235                 240
Glu Ala Arg Gln Gln Arg Phe Ala His Phe Thr Glu Leu Ala Ile Val
                245                 250                 255
Ser Val Gln Glu Ile Val Asp Phe Ala Lys Gln Leu Pro Gly Phe Leu
            260                 265                 270
Gln Leu Ser Arg Glu Asp Gln Ile Ala Leu Leu Lys Thr Ser Ala Ile
        275                 280                 285
Glu Val Met Leu Leu Glu Thr Ser Arg Arg Tyr Asn Pro Gly Ser Glu
    290                 295                 300
Ser Ile Thr Phe Leu Lys Asp Phe Ser Tyr Asn Arg Glu Asp Phe Ala
305                 310                 315                 320
Lys Ala Gly Leu Gln Val Glu Phe Ile Asn Pro Ile Phe Glu Phe Ser
                325                 330                 335
Arg Ala Met Asn Glu Leu Gln Leu Asn Asp Ala Glu Phe Ala Leu Leu
            340                 345                 350
Ile Ala Ile Ser Ile Phe Ser Ala Asp Arg Pro Asn Val Gln Asp Gln
        355                 360                 365
Leu Gln Val Glu Arg Leu Gln His Thr Tyr Val Glu Ala Leu His Ala
    370                 375                 380
```

```
Tyr Val Ser Ile His His Pro His Asp Arg Leu Met Phe Pro Arg Met
385             390             395             400

Leu Met Lys Leu Val Ser Leu Arg Thr Leu Ser Ser Val His Ser Glu
                405             410             415

Gln Val Phe Ala Leu Arg Leu Gln Asp Lys Lys Leu Pro Pro Leu Leu
            420             425             430

Ser Glu Ile Trp Asp Val His Glu
        435             440
```

( 2 ) INFORMATION FOR SEQ ID NO:9:

( i ) SEQUENCE CHARACTERISTICS:
        ( A ) LENGTH: 2009 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR4 (XR4.SEQ)

( i x ) FEATURE:
        ( A ) NAME/KEY: CDS
        ( B ) LOCATION: 263..1582

( x i ) SEQUENCE DESCRIPTION: SEQ ID NO:9:

```
GAATTCCCTG GGGATTAATG GGAAAAGTTT TGGCAGGAGC TGGGGGATTC TGCGGAGCCT      60

GCGGGACGGC GGCAGCGGCG CGAGAGGCGG CCGGGACAGT GCTGTGCAGC GGTGTGGGTA     120

TGCGCATGGG ACTCACTCAG AGGCTCCTGC TCACTGACAG ATGAAGACAA ACCCACGGTA     180

AAGGCAGTCC ATCTGCGCTC AGACCCAGAT GGTGGCAGAG CTATGACCAG GCCTGCAGCG     240

CCACGCCAAG TGGGGGTCAG TC ATG GAA CAG CCA CAG GAG GAG ACC CCT GAG      292
                         Met Glu Gln Pro Gln Glu Glu Thr Pro Glu
                         1               5                   10

GCC CGG GAA GAG GAG AAA GAG GAA GTG GCC ATG GGT GAC GGA GCC CCG      340
Ala Arg Glu Glu Glu Lys Glu Glu Val Ala Met Gly Asp Gly Ala Pro
                15                  20                  25

GAG CTC AAT GGG GGA CCA GAA CAC ACG CTT CCT TCC AGC AGC TGT GCA      388
Glu Leu Asn Gly Gly Pro Glu His Thr Leu Pro Ser Ser Ser Cys Ala
            30                  35                  40

GAC CTC TCC CAG AAT TCC TCC CCT TCC TCC CTG CTG GAC CAG CTG CAG      436
Asp Leu Ser Gln Asn Ser Ser Pro Ser Ser Leu Leu Asp Gln Leu Gln
        45                  50                  55

ATG GGC TGT GAT GGG GCC TCA GGC GGC AGC CTC AAC ATG GAA TGT CGG      484
Met Gly Cys Asp Gly Ala Ser Gly Gly Ser Leu Asn Met Glu Cys Arg
    60                  65                  70

GTG TGC GGG GAC AAG GCC TCG GGC TTC CAC TAC GGG GTC CAC GCG TGC      532
Val Cys Gly Asp Lys Ala Ser Gly Phe His Tyr Gly Val His Ala Cys
75                  80                  85                  90

GAG GGG TGC AAG GGC TTC TTC CGC CGG ACA ATC CGC ATG AAG CTC GAG      580
Glu Gly Cys Lys Gly Phe Phe Arg Arg Thr Ile Arg Met Lys Leu Glu
                95                  100                 105

TAT GAG AAG TGC GAT CGG ATC TGC AAG ATC CAG AAG AAG AAC CGC AAC      628
Tyr Glu Lys Cys Asp Arg Ile Cys Lys Ile Gln Lys Lys Asn Arg Asn
            110                 115                 120

AAG TGT CAG TAC TGC CGC TTC CAG AAG TGC CTG GCA CTC GGC ATG TCG      676
Lys Cys Gln Tyr Cys Arg Phe Gln Lys Cys Leu Ala Leu Gly Met Ser
        125                 130                 135

CAC AAC GCT ATC CGC TTT GGA CGG ATG CCG GAC GGC GAG AAG AGG AAG      724
His Asn Ala Ile Arg Phe Gly Arg Met Pro Asp Gly Glu Lys Arg Lys
    140                 145                 150
```

| | | | | | | | | | | | | | | | | |
|---|---|---|---|---|---|---|---|---|---|---|---|---|---|---|---|---|
| CTG | GTG | GCG | GGG | CTG | ACT | GCC | AGC | GAG | GGG | TGC | CAG | CAC | AAC | CCC | CAG | 772 |
| Leu | Val | Ala | Gly | Leu | Thr | Ala | Ser | Glu | Gly | Cys | Gln | His | Asn | Pro | Gln | |
| 155 | | | | 160 | | | | | 165 | | | | | 170 | | |
| CTG | GCC | GAC | CTG | AAG | GCC | TTC | TCT | AAG | CAC | ATC | TAC | AAC | GCC | TAC | CTG | 820 |
| Leu | Ala | Asp | Leu | Lys | Ala | Phe | Ser | Lys | His | Ile | Tyr | Asn | Ala | Tyr | Leu | |
| | | | | 175 | | | | | 180 | | | | | 185 | | |
| AAA | AAC | TTC | AAC | ATG | ACC | AAA | AAG | AAG | GCC | CGG | AGC | ATC | CTC | ACC | GGC | 868 |
| Lys | Asn | Phe | Asn | Met | Thr | Lys | Lys | Lys | Ala | Arg | Ser | Ile | Leu | Thr | Gly | |
| | | | 190 | | | | | 195 | | | | | 200 | | | |
| AAG | TCC | AGC | CAC | AAC | GCA | CCC | TTT | GTC | ATC | CAC | GAC | ATC | GAG | ACA | CTG | 916 |
| Lys | Ser | Ser | His | Asn | Ala | Pro | Phe | Val | Ile | His | Asp | Ile | Glu | Thr | Leu | |
| | | 205 | | | | | 210 | | | | | 215 | | | | |
| TGG | CAG | GCA | GAG | AAG | GGC | CTG | GTG | TGG | AAA | CAG | CTG | GTG | AAC | GTG | CCG | 964 |
| Trp | Gln | Ala | Glu | Lys | Gly | Leu | Val | Trp | Lys | Gln | Leu | Val | Asn | Val | Pro | |
| 220 | | | | | 225 | | | | | 230 | | | | | | |
| CCC | TAC | AAC | GAG | ATC | AGT | GTG | CAC | GTG | TTC | TAC | CGC | TGC | CAG | TCC | ACC | 1012 |
| Pro | Tyr | Asn | Glu | Ile | Ser | Val | His | Val | Phe | Tyr | Arg | Cys | Gln | Ser | Thr | |
| 235 | | | | | 240 | | | | | 245 | | | | | 250 | |
| ACA | GTG | GAG | ACA | GTC | CGA | GAG | CTC | ACC | GAG | TTC | GCC | AAG | AAC | ATC | CCC | 1060 |
| Thr | Val | Glu | Thr | Val | Arg | Glu | Leu | Thr | Glu | Phe | Ala | Lys | Asn | Ile | Pro | |
| | | | | 255 | | | | | 260 | | | | | 265 | | |
| AAC | TTC | AGC | AGC | CTC | TTC | CTC | AAT | GAC | CAG | GTG | ACC | CTC | CTC | AAG | TAT | 1108 |
| Asn | Phe | Ser | Ser | Leu | Phe | Leu | Asn | Asp | Gln | Val | Thr | Leu | Leu | Lys | Tyr | |
| | | | 270 | | | | | 275 | | | | | 280 | | | |
| GGC | GTG | CAC | GAG | GCC | ATC | TTT | GCC | ATG | CTG | GCC | TCC | ATC | GTC | AAC | AAA | 1156 |
| Gly | Val | His | Glu | Ala | Ile | Phe | Ala | Met | Leu | Ala | Ser | Ile | Val | Asn | Lys | |
| | | 285 | | | | | 290 | | | | | 295 | | | | |
| GAC | GGG | CTG | CTG | GTG | GCC | AAC | GGC | AGT | GGC | TTC | GTC | ACC | CAC | GAG | TTC | 1204 |
| Asp | Gly | Leu | Leu | Val | Ala | Asn | Gly | Ser | Gly | Phe | Val | Thr | His | Glu | Phe | |
| | 300 | | | | | 305 | | | | | 310 | | | | | |
| TTG | CGA | AGT | CTC | CGC | AAG | CCC | TTC | AGT | GAC | ATC | ATT | GAG | CCC | AAG | TTC | 1252 |
| Leu | Arg | Ser | Leu | Arg | Lys | Pro | Phe | Ser | Asp | Ile | Ile | Glu | Pro | Lys | Phe | |
| 315 | | | | | 320 | | | | | 325 | | | | | 330 | |
| GAG | TTT | GCT | GTC | AAG | TTC | AAT | GCG | CTG | GAG | CTC | GAT | GAC | AGT | GAC | CTG | 1300 |
| Glu | Phe | Ala | Val | Lys | Phe | Asn | Ala | Leu | Glu | Leu | Asp | Asp | Ser | Asp | Leu | |
| | | | | 335 | | | | | 340 | | | | | 345 | | |
| GCG | CTC | TTC | ATC | GCG | GCC | ATC | ATT | CTG | TGT | GGA | GAC | CGG | CCA | GGC | CTC | 1348 |
| Ala | Leu | Phe | Ile | Ala | Ala | Ile | Ile | Leu | Cys | Gly | Asp | Arg | Pro | Gly | Leu | |
| | | | 350 | | | | | 355 | | | | | 360 | | | |
| ATG | AAT | GTG | CCC | CAG | GTA | GAA | GCC | ATC | CAG | GAC | ACC | ATT | CTG | CGG | GCT | 1396 |
| Met | Asn | Val | Pro | Gln | Val | Glu | Ala | Ile | Gln | Asp | Thr | Ile | Leu | Arg | Ala | |
| | | 365 | | | | | 370 | | | | | 375 | | | | |
| CTA | GAA | TTC | CAT | CTG | CAG | GTC | AAC | CAC | CCT | GAC | AGC | CAG | TAC | CTC | TTC | 1444 |
| Leu | Glu | Phe | His | Leu | Gln | Val | Asn | His | Pro | Asp | Ser | Gln | Tyr | Leu | Phe | |
| | 380 | | | | | 385 | | | | | 390 | | | | | |
| CCC | AAG | CTG | CTG | CAG | AAG | ATG | GCA | GAC | CTG | CGG | CAC | GTG | GTC | ACT | GAG | 1492 |
| Pro | Lys | Leu | Leu | Gln | Lys | Met | Ala | Asp | Leu | Arg | His | Val | Val | Thr | Glu | |
| 395 | | | | | 400 | | | | | 405 | | | | | 410 | |
| CAT | GCC | CAG | ATG | ATG | CAG | TGG | CTA | AAG | AAG | ACG | GAG | AGT | GAG | ACC | TTG | 1540 |
| His | Ala | Gln | Met | Met | Gln | Trp | Leu | Lys | Lys | Thr | Glu | Ser | Glu | Thr | Leu | |
| | | | | 415 | | | | | 420 | | | | | 425 | | |
| CTG | CAC | CCC | CTG | CTC | CAG | GAA | ATC | TAC | AAG | GAC | ATG | TAC | TAAGGCCGCA | | | 1589 |
| Leu | His | Pro | Leu | Leu | Gln | Glu | Ile | Tyr | Lys | Asp | Met | Tyr | | | | |
| | | | 430 | | | | | 435 | | | | | 440 | | | |

```
GCCCAGGCCT CCCCTCAGGC TCTGCTGGGC CCAGCCACGG ACTGTTCAGA GGACCAGCCA    1649

CAGGCACTGG CAGTCAAGCA GCTAGAGCCT ACTCACAACA CTCCAGACAC GTGGCCAGA     1709

CTCTTCCCCC AACACCCCCA CCCCCACCAA CCCCCCCATT CCCCCAACCC CCCTCCCCCA    1769

CCCCGCTCTC CCCATGGCCC GTTTCCTGTT TCTCCTCAGC ACCTCCTGTT CTTGCTGTCT    1829
```

```
CCCTAGCGCC CTTGCTCCCC CCCCTTTGCC TTCCTTCTCT AGCATCCCCC TCCTCCCAGT    1889
CCTCACATTT GTCTGATTCA CAGCAGACAG CCCGTTGGTA CGCTCACCAG CAGCCTAAAA    1949
GCAGTGGGCC TGTGCTGGCC CAGTCCTGCC TCTCCTCTCT ATCCCCTTCA AAGGGAATTC    2009
```

( 2 ) INFORMATION FOR SEQ ID NO:10:

( i ) SEQUENCE CHARACTERISTICS:
        ( A ) LENGTH: 439 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Glu Gln Pro Gln Glu Glu Thr Pro Glu Ala Arg Glu Glu Lys
 1               5                  10                  15
Glu Glu Val Ala Met Gly Asp Gly Ala Pro Glu Leu Asn Gly Gly Pro
            20                  25                  30
Glu His Thr Leu Pro Ser Ser Ser Cys Ala Asp Leu Ser Gln Asn Ser
        35                  40                  45
Ser Pro Ser Ser Leu Leu Asp Gln Leu Gln Met Gly Cys Asp Gly Ala
    50                  55                  60
Ser Gly Gly Ser Leu Asn Met Glu Cys Arg Val Cys Gly Asp Lys Ala
65                  70                  75                  80
Ser Gly Phe His Tyr Gly Val His Ala Cys Glu Gly Cys Lys Gly Phe
                85                  90                  95
Phe Arg Arg Thr Ile Arg Met Lys Leu Glu Tyr Glu Lys Cys Asp Arg
            100                 105                 110
Ile Cys Lys Ile Gln Lys Lys Asn Arg Asn Lys Cys Gln Tyr Cys Arg
        115                 120                 125
Phe Gln Lys Cys Leu Ala Leu Gly Met Ser His Asn Ala Ile Arg Phe
    130                 135                 140
Gly Arg Met Pro Asp Gly Glu Lys Arg Lys Leu Val Ala Gly Leu Thr
145                 150                 155                 160
Ala Ser Glu Gly Cys Gln His Asn Pro Gln Leu Ala Asp Leu Lys Ala
                165                 170                 175
Phe Ser Lys His Ile Tyr Asn Ala Tyr Leu Lys Asn Phe Asn Met Thr
            180                 185                 190
Lys Lys Lys Ala Arg Ser Ile Leu Thr Gly Lys Ser Ser His Asn Ala
        195                 200                 205
Pro Phe Val Ile His Asp Ile Glu Thr Leu Trp Gln Ala Glu Lys Gly
    210                 215                 220
Leu Val Trp Lys Gln Leu Val Asn Val Pro Pro Tyr Asn Glu Ile Ser
225                 230                 235                 240
Val His Val Phe Tyr Arg Cys Gln Ser Thr Thr Val Glu Thr Val Arg
                245                 250                 255
Glu Leu Thr Glu Phe Ala Lys Asn Ile Pro Asn Phe Ser Ser Leu Phe
            260                 265                 270
Leu Asn Asp Gln Val Thr Leu Leu Lys Tyr Gly Val His Glu Ala Ile
        275                 280                 285
Phe Ala Met Leu Ala Ser Ile Val Asn Lys Asp Gly Leu Leu Val Ala
    290                 295                 300
Asn Gly Ser Gly Phe Val Thr His Glu Phe Leu Arg Ser Leu Arg Lys
305                 310                 315                 320
Pro Phe Ser Asp Ile Ile Glu Pro Lys Phe Glu Phe Ala Val Lys Phe
```

|  |  |  | 325 |  |  |  | 330 |  |  |  | 335 |  |  |
|---|---|---|---|---|---|---|---|---|---|---|---|---|---|
| Asn | Ala | Leu | Glu | Leu | Asp | Asp | Ser | Asp | Leu | Ala | Leu | Phe | Ile | Ala | Ala |
|  |  |  | 340 |  |  |  | 345 |  |  |  | 350 |  |  |
| Ile | Ile | Leu | Cys | Gly | Asp | Arg | Pro | Gly | Leu | Met | Asn | Val | Pro | Gln | Val |
|  |  |  | 355 |  |  |  | 360 |  |  |  | 365 |  |  |
| Glu | Ala | Ile | Gln | Asp | Thr | Ile | Leu | Arg | Ala | Leu | Glu | Phe | His | Leu | Gln |
|  |  |  | 370 |  |  |  | 375 |  |  |  | 380 |  |  |
| Val | Asn | His | Pro | Asp | Ser | Gln | Tyr | Leu | Phe | Pro | Lys | Leu | Leu | Gln | Lys |
| 385 |  |  |  | 390 |  |  |  | 395 |  |  |  | 400 |
| Met | Ala | Asp | Leu | Arg | His | Val | Val | Thr | Glu | His | Ala | Gln | Met | Met | Gln |
|  |  |  | 405 |  |  |  | 410 |  |  |  | 415 |  |  |
| Trp | Leu | Lys | Lys | Thr | Glu | Ser | Glu | Thr | Leu | Leu | His | Pro | Leu | Leu | Gln |
|  |  |  | 420 |  |  |  | 425 |  |  |  | 430 |  |  |
| Glu | Ile | Tyr | Lys | Asp | Met | Tyr |
|  |  |  | 435 |  |  |  |

( 2 ) INFORMATION FOR SEQ ID NO:11:

( i ) SEQUENCE CHARACTERISTICS:
        ( A ) LENGTH: 2468 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR5 (XR5.SEQ)

( i x ) FEATURE:
        ( A ) NAME/KEY: CDS
        ( B ) LOCATION: 1..1677

( x i ) SEQUENCE DESCRIPTION: SEQ ID NO:11:

| GAA | TTC | CGG | CGC | GGA | GGG | GCG | CGG | CGC | GAG | GGG | CCG | GAG | CCG | GGC | GGC | 48 |
|---|---|---|---|---|---|---|---|---|---|---|---|---|---|---|---|---|
| Glu | Phe | Arg | Arg | Gly | Gly | Ala | Arg | Arg | Glu | Gly | Pro | Glu | Pro | Gly | Gly |  |
| 1 |  |  |  | 5 |  |  |  |  | 10 |  |  |  |  | 15 |  |  |

| TCA | GGG | GCC | CAG | AGA | GTG | CGG | CGG | CCG | AGA | GCC | TGC | CGG | CCC | CTG | ACA | 96 |
|---|---|---|---|---|---|---|---|---|---|---|---|---|---|---|---|---|
| Ser | Gly | Ala | Gln | Arg | Val | Arg | Arg | Pro | Arg | Ala | Cys | Arg | Pro | Leu | Thr |  |
|  |  |  | 20 |  |  |  |  | 25 |  |  |  |  | 30 |  |  |  |

| GCC | CCC | TCC | CCC | CGT | GGA | AGA | CCA | GGA | CGA | CGA | CTA | CGA | AGG | CGC | AAG | 144 |
|---|---|---|---|---|---|---|---|---|---|---|---|---|---|---|---|---|
| Ala | Pro | Ser | Pro | Arg | Gly | Arg | Pro | Gly | Arg | Arg | Leu | Arg | Arg | Arg | Lys |  |
|  |  | 35 |  |  |  |  | 40 |  |  |  |  | 45 |  |  |  |  |

| TCA | TGG | CGG | AGC | AGC | GAA | CGC | CGA | GAG | GGC | CCT | GAG | CAC | CGC | CGC | ATG | 192 |
|---|---|---|---|---|---|---|---|---|---|---|---|---|---|---|---|---|
| Ser | Trp | Arg | Ser | Ser | Glu | Arg | Arg | Glu | Gly | Pro | Glu | His | Arg | Arg | Met |  |
| 50 |  |  |  |  | 55 |  |  |  |  | 60 |  |  |  |  |  |  |

| GAG | CGG | GAC | GAA | CGG | CCA | CCT | AGC | GGA | GGG | GGA | GGC | GGC | GGG | GGC | TCG | 240 |
|---|---|---|---|---|---|---|---|---|---|---|---|---|---|---|---|---|
| Glu | Arg | Asp | Glu | Arg | Pro | Pro | Ser | Gly | Gly | Gly | Gly | Gly | Gly | Gly | Ser |  |
| 65 |  |  |  |  | 70 |  |  |  |  | 75 |  |  |  |  | 80 |  |

| GCG | GGG | TTC | CTG | GAG | CCG | CCC | GCC | GCG | CTC | CCT | CCG | CCG | CCG | CGC | AAC | 288 |
|---|---|---|---|---|---|---|---|---|---|---|---|---|---|---|---|---|
| Ala | Gly | Phe | Leu | Glu | Pro | Pro | Ala | Ala | Leu | Pro | Pro | Pro | Pro | Arg | Asn |  |
|  |  |  |  | 85 |  |  |  |  | 90 |  |  |  |  | 95 |  |  |

| GGT | TTC | TGT | CAG | GAT | GAA | TTG | GCA | GAG | CTT | GAT | CCA | GGC | ACT | AAT | GGA | 336 |
|---|---|---|---|---|---|---|---|---|---|---|---|---|---|---|---|---|
| Gly | Phe | Cys | Gln | Asp | Glu | Leu | Ala | Glu | Leu | Asp | Pro | Gly | Thr | Asn | Gly |  |
|  |  |  | 100 |  |  |  |  | 105 |  |  |  |  | 110 |  |  |  |

| GAG | ACT | GAC | AGT | TTA | ACA | CTT | GGC | CAA | GGC | CAT | ATA | CCT | GTT | TCC | GTC | 384 |
|---|---|---|---|---|---|---|---|---|---|---|---|---|---|---|---|---|
| Glu | Thr | Asp | Ser | Leu | Thr | Leu | Gly | Gln | Gly | His | Ile | Pro | Val | Ser | Val |  |
|  |  | 115 |  |  |  |  | 120 |  |  |  |  | 125 |  |  |  |  |

| CCA | GAT | GAT | CGA | GCT | GAA | CAA | CGA | ACC | TGT | CTC | ATC | TGT | GGG | GAC | CGC | 432 |
|---|---|---|---|---|---|---|---|---|---|---|---|---|---|---|---|---|
| Pro | Asp | Asp | Arg | Ala | Glu | Gln | Arg | Thr | Cys | Leu | Ile | Cys | Gly | Asp | Arg |  |
|  | 130 |  |  |  |  | 135 |  |  |  |  | 140 |  |  |  |  |  |

| GCT | ACG | GGC | TTG | CAC | TAT | GGG | ATC | ATC | TCC | TGC | GAG | GGC | TGC | AAG | GGG | 480 |

| | | | | | | | | | | | | | | | | |
|---|---|---|---|---|---|---|---|---|---|---|---|---|---|---|---|---|
| Ala | Thr | Gly | Leu | His | Tyr | Gly | Ile | Ile | Ser | Cys | Glu | Gly | Cys | Lys | Gly | |
| 145 | | | | 150 | | | | | 155 | | | | | 160 | | |
| TTT | TTC | AAG | AGG | AGC | ATT | TGC | AAC | AAA | CGG | GTG | TAT | CGG | TGC | AGT | CGT | 528 |
| Phe | Phe | Lys | Arg | Ser | Ile | Cys | Asn | Lys | Arg | Val | Tyr | Arg | Cys | Ser | Arg | |
| | | | | 165 | | | | | 170 | | | | | 175 | | |
| GAC | AAG | AAC | TGT | GTC | ATG | TCC | CGG | AAG | CAG | AGG | AAC | AGA | TGT | CAG | TAC | 576 |
| Asp | Lys | Asn | Cys | Val | Met | Ser | Arg | Lys | Gln | Arg | Asn | Arg | Cys | Gln | Tyr | |
| | | | 180 | | | | | 185 | | | | | 190 | | | |
| TGC | CGC | CTG | CTC | AAG | TGT | CTC | CAG | ATG | GGC | ATG | AAC | AGG | AAG | GCT | ATC | 624 |
| Cys | Arg | Leu | Leu | Lys | Cys | Leu | Gln | Met | Gly | Met | Asn | Arg | Lys | Ala | Ile | |
| | | 195 | | | | | 200 | | | | | 205 | | | | |
| AGA | GAA | GAT | GGC | ATG | CCT | GGA | GGC | CGG | AAC | AAG | AGC | ATT | GGA | CCA | GTC | 672 |
| Arg | Glu | Asp | Gly | Met | Pro | Gly | Gly | Arg | Asn | Lys | Ser | Ile | Gly | Pro | Val | |
| 210 | | | | | 215 | | | | | 220 | | | | | | |
| CAG | ATA | TCA | GAA | GAA | GAA | ATT | GAA | AGA | ATC | ATG | TCT | GGA | CAG | GAG | TTT | 720 |
| Gln | Ile | Ser | Glu | Glu | Glu | Ile | Glu | Arg | Ile | Met | Ser | Gly | Gln | Glu | Phe | |
| 225 | | | | | 230 | | | | | 235 | | | | | 240 | |
| GAG | GAA | GAA | GCC | AAT | CAC | TGG | AGC | AAC | CAT | GGT | GAC | AGC | GAC | CAC | AGT | 768 |
| Glu | Glu | Glu | Ala | Asn | His | Trp | Ser | Asn | His | Gly | Asp | Ser | Asp | His | Ser | |
| | | | | 245 | | | | | 250 | | | | | 255 | | |
| TCC | CCT | GGG | AAC | AGG | GCT | TCA | GAG | AGC | AAC | CAG | CCC | TCA | CCA | GGC | TCC | 816 |
| Ser | Pro | Gly | Asn | Arg | Ala | Ser | Glu | Ser | Asn | Gln | Pro | Ser | Pro | Gly | Ser | |
| | | | | 260 | | | | | 265 | | | | | 270 | | |
| ACA | CTA | TCA | TCC | AGT | AGG | TCT | GTG | GAA | CTA | AAT | GGA | TTC | ATG | GCA | TTC | 864 |
| Thr | Leu | Ser | Ser | Ser | Arg | Ser | Val | Glu | Leu | Asn | Gly | Phe | Met | Ala | Phe | |
| | | 275 | | | | | 280 | | | | | 285 | | | | |
| AGG | GAT | CAG | TAC | ATG | GGG | ATG | TCA | GTG | CCT | CCA | CAT | TAT | CAA | TAC | ATA | 912 |
| Arg | Asp | Gln | Tyr | Met | Gly | Met | Ser | Val | Pro | Pro | His | Tyr | Gln | Tyr | Ile | |
| 290 | | | | | 295 | | | | | 300 | | | | | | |
| CCA | CAC | CTT | TTT | AGC | TAT | TCT | GGC | CAC | TCA | CCA | CTT | TTG | CCC | CCA | CAA | 960 |
| Pro | His | Leu | Phe | Ser | Tyr | Ser | Gly | His | Ser | Pro | Leu | Leu | Pro | Pro | Gln | |
| 305 | | | | | 310 | | | | | 315 | | | | | 320 | |
| GCT | CGA | AGC | CTG | GAC | CCT | CAG | TCC | TAC | AGT | CTG | ATT | CAT | CAG | CTG | ATG | 1008 |
| Ala | Arg | Ser | Leu | Asp | Pro | Gln | Ser | Tyr | Ser | Leu | Ile | His | Gln | Leu | Met | |
| | | | | 325 | | | | | 330 | | | | | 335 | | |
| TCA | GCC | GAA | GAC | CTG | GAG | CCA | TTG | GGC | ACA | CCT | ATG | TTG | ATT | GAA | GAT | 1056 |
| Ser | Ala | Glu | Asp | Leu | Glu | Pro | Leu | Gly | Thr | Pro | Met | Leu | Ile | Glu | Asp | |
| | | | 340 | | | | | 345 | | | | | 350 | | | |
| GGG | TAT | GCT | GTG | ACA | CAG | GCA | GAA | CTG | TTT | GCT | CTG | CTT | TGC | CGC | CTG | 1104 |
| Gly | Tyr | Ala | Val | Thr | Gln | Ala | Glu | Leu | Phe | Ala | Leu | Leu | Cys | Arg | Leu | |
| | | 355 | | | | | 360 | | | | | 365 | | | | |
| GCC | GAC | GAG | TTG | CTC | TTT | AGG | CAG | ATT | GCC | TGG | ATC | AAG | AAG | CTG | CCT | 1152 |
| Ala | Asp | Glu | Leu | Leu | Phe | Arg | Gln | Ile | Ala | Trp | Ile | Lys | Lys | Leu | Pro | |
| 370 | | | | | 375 | | | | | 380 | | | | | | |
| TTC | TTC | TGC | GAG | CTC | TCA | ATC | AAG | GAT | TAC | ACG | TGC | CTC | TTG | AGC | TCT | 1200 |
| Phe | Phe | Cys | Glu | Leu | Ser | Ile | Lys | Asp | Tyr | Thr | Cys | Leu | Leu | Ser | Ser | |
| 385 | | | | | 390 | | | | | 395 | | | | | 400 | |
| ACG | TGG | CAG | GAG | TTA | ATC | CTG | CTC | TCC | TCC | CTC | ACA | GTG | TAC | AGC | AAG | 1248 |
| Thr | Trp | Gln | Glu | Leu | Ile | Leu | Leu | Ser | Ser | Leu | Thr | Val | Tyr | Ser | Lys | |
| | | | | 405 | | | | | 410 | | | | | 415 | | |
| CAG | ATC | TTT | GGG | GAG | CTG | GCT | GAT | GTC | ACA | GCC | AAG | TAC | TCA | CCC | TCT | 1296 |
| Gln | Ile | Phe | Gly | Glu | Leu | Ala | Asp | Val | Thr | Ala | Lys | Tyr | Ser | Pro | Ser | |
| | | | 420 | | | | | 425 | | | | | 430 | | | |
| GAT | GAA | GAA | CTC | CAC | AGA | TTT | AGT | GAT | GAA | GGG | ATG | GAG | GTG | ATT | GAA | 1344 |
| Asp | Glu | Glu | Leu | His | Arg | Phe | Ser | Asp | Glu | Gly | Met | Glu | Val | Ile | Glu | |
| | | | | 435 | | | | | 440 | | | | | 445 | | |
| CGA | CTC | ATC | TAC | CTA | TAT | CAC | AAG | TTC | CAT | CAG | CTG | AAG | GTC | AGC | AAC | 1392 |
| Arg | Leu | Ile | Tyr | Leu | Tyr | His | Lys | Phe | His | Gln | Leu | Lys | Val | Ser | Asn | |
| | | 450 | | | | | 455 | | | | | 460 | | | | |
| GAG | GAG | TAC | GCA | TGC | ATG | AAA | GCA | ATT | AAC | TTC | CTG | AAT | CAA | GAT | ATC | 1440 |

|     |     |     |     |     |     |     |     |     |     |     |     |     |     |      |
|-----|-----|-----|-----|-----|-----|-----|-----|-----|-----|-----|-----|-----|-----|------|
| Glu | Glu | Tyr | Ala | Cys | Met | Lys | Ala | Ile | Asn | Phe | Leu | Asn | Gln | Asp Ile |
| 465 |     |     |     |     | 470 |     |     |     |     | 475 |     |     |     | 480 |

| AGG | GGT | CTG | ACC | AGT | GCC | TCA | CAG | CTG | GAA | CAA | CTG | AAC | AAG | CGG | TAT | 1488 |
|-----|-----|-----|-----|-----|-----|-----|-----|-----|-----|-----|-----|-----|-----|-----|-----|------|
| Arg | Gly | Leu | Thr | Ser | Ala | Ser | Gln | Leu | Glu | Gln | Leu | Asn | Lys | Arg | Tyr |      |
|     |     |     |     | 485 |     |     |     |     | 490 |     |     |     |     | 495 |     |      |

| TGG | TAC | ATT | TGT | CAG | GAT | TTC | ACT | GAA | TAT | AAA | TAC | ACA | CAT | CAG | CCA | 1536 |
|-----|-----|-----|-----|-----|-----|-----|-----|-----|-----|-----|-----|-----|-----|-----|-----|------|
| Trp | Tyr | Ile | Cys | Gln | Asp | Phe | Thr | Glu | Tyr | Lys | Tyr | Thr | His | Gln | Pro |      |
|     |     |     |     | 500 |     |     |     |     | 505 |     |     |     |     | 510 |     |      |

| AAC | CGC | TTT | CCT | GAT | CTT | ATG | ATG | TGC | TTG | CCA | GAG | ATC | CGA | TAC | ATC | 1584 |
|-----|-----|-----|-----|-----|-----|-----|-----|-----|-----|-----|-----|-----|-----|-----|-----|------|
| Asn | Arg | Phe | Pro | Asp | Leu | Met | Met | Cys | Leu | Pro | Glu | Ile | Arg | Tyr | Ile |      |
|     |     |     |     |     |     | 520 |     |     |     |     |     | 525 |     |     |     |      |
|     |     | 515 |     |     |     |     |     |     |     |     |     |     |     |     |     |      |

| GCA | GGC | AAG | ATG | GTG | AAT | GTG | CCC | CTG | GAG | CAG | CTG | CCC | CTC | CTC | TTT | 1632 |
|-----|-----|-----|-----|-----|-----|-----|-----|-----|-----|-----|-----|-----|-----|-----|-----|------|
| Ala | Gly | Lys | Met | Val | Asn | Val | Pro | Leu | Glu | Gln | Leu | Pro | Leu | Leu | Phe |      |
|     |     | 530 |     |     |     |     | 535 |     |     |     |     | 540 |     |     |     |      |

| AAG | GTG | GTG | CTG | CAC | TCC | TGC | AAG | ACA | AGT | ACG | GTG | AAG | GAG | TGACCTGTGC | 1684 |
|-----|-----|-----|-----|-----|-----|-----|-----|-----|-----|-----|-----|-----|-----|------------|------|
| Lys | Val | Val | Leu | His | Ser | Cys | Lys | Thr | Ser | Thr | Val | Lys | Glu |            |      |
| 545 |     |     |     |     | 550 |     |     |     |     | 555 |     |     |     |            |      |

| CCTGCACCTC | CTTGGGCCAC | CCACAGTGCC | TTGGGTAGGC | AGCACAGGCT | CCAGAGGAAA | 1744 |
|------------|------------|------------|------------|------------|------------|------|
| GAGCCAGAGA | CCAAGATGGA | GACTGTGGAG | CAGCTACCTC | CATCACAAGA | AGAATTTGTT | 1804 |
| TGTTTGTCTG | TTTTTAACCT | CATTTTTCTA | TATATTTATT | TCACGACAGA | GTTGAATGTA | 1864 |
| TGGCCTTCAA | CATGATGCAC | ATGCTTTTGT | GTGAATGCAG | CAGATGCATT | TCCTTGCAGT | 1924 |
| TTACAGAATG | TGAAGATGTT | TAATGTTACC | GTGTTGTCAT | TGTTTAGAGA | TAGGTTTTTT | 1984 |
| TGTATTTTGA | TGGAGAGGGT | AGGATGGACT | AGATGAGTAT | TCCATAATG  | TTGACAAAGA | 2044 |
| CAACTACCTC | AATGGAAACA | GGTGTATGAC | CATCCCTACC | TTTTTCCACA | TTTTCTCAGC | 2104 |
| AGATACACAC | TTGTCTGTTA | GAGAGCAAAC | TGCCTTTTTT | ATAGCCACAG | ACTTCTAAGT | 2164 |
| AAAAGAAGCA | AACAAAGGAG | CGAAGTGGTA | TAGGGAGATT | TACTAATGGC | CAGTTGGGAC | 2224 |
| ATCTGAGAGG | CAATTTGATT | TTGATCATCT | CATCCCACAA | GCCTGAAGGC | AGAAACTCTG | 2284 |
| CCTTACCTTC | TGCTGCACCC | CTCCCCCCCC | CCACACGCTG | TTGTCTGTTG | ATGCTGCTGT | 2344 |
| CAAGTTTTCA | TCCAGGTAGA | GTCCTAACAA | TAAGCCAGTA | TGTAGGACTT | GCCTCCCAGC | 2404 |
| GCCCTTGTAG | CTCATAGCTG | CCTAGTTTGC | TGTTCTAGAT | CTACCAAGGC | CTACTTCGGA | 2464 |
| ATTC       |            |            |            |            |            | 2468 |

( 2 ) INFORMATION FOR SEQ ID NO:12:

( i ) SEQUENCE CHARACTERISTICS:
        ( A ) LENGTH: 558 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Glu | Phe | Arg | Arg | Gly | Gly | Ala | Arg | Arg | Glu | Gly | Pro | Glu | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Gly | Ala | Gln | Arg | Val | Arg | Arg | Pro | Arg | Ala | Cys | Arg | Pro | Leu | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Pro | Ser | Pro | Arg | Gly | Arg | Pro | Gly | Arg | Arg | Leu | Arg | Arg | Arg | Lys |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Trp | Arg | Ser | Ser | Glu | Arg | Arg | Glu | Gly | Pro | Glu | His | Arg | Arg | Met |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Arg | Asp | Glu | Arg | Pro | Pro | Ser | Gly | Gly | Gly | Gly | Gly | Gly | Gly | Ser |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Gly | Phe | Leu | Glu | Pro | Pro | Ala | Ala | Leu | Pro | Pro | Pro | Pro | Arg | Asn |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| | | | | | | | | | | | | | | | |
|---|---|---|---|---|---|---|---|---|---|---|---|---|---|---|---|
|Gly|Phe|Cys|Gln|Asp|Glu|Leu|Ala|Glu|Leu|Asp|Pro|Gly|Thr|Asn|Gly|
| | | |100| | | |105| | | |110| | | | |
|Glu|Thr|Asp|Ser|Leu|Thr|Leu|Gly|Gln|Gly|His|Ile|Pro|Val|Ser|Val|
| | |115| | | |120| | | | |125| | | | |
|Pro|Asp|Asp|Arg|Ala|Glu|Gln|Arg|Thr|Cys|Leu|Ile|Cys|Gly|Asp|Arg|
| |130| | | | |135| | | |140| | | | | |
|Ala|Thr|Gly|Leu|His|Tyr|Gly|Ile|Ile|Ser|Cys|Glu|Gly|Cys|Lys|Gly|
|145| | | | |150| | | |155| | | | | |160|
|Phe|Phe|Lys|Arg|Ser|Ile|Cys|Asn|Lys|Arg|Val|Tyr|Arg|Cys|Ser|Arg|
| | | |165| | | |170| | | |175| | | | |
|Asp|Lys|Asn|Cys|Val|Met|Ser|Arg|Lys|Gln|Arg|Asn|Arg|Cys|Gln|Tyr|
| | |180| | | |185| | | | |190| | | | |
|Cys|Arg|Leu|Leu|Lys|Cys|Leu|Gln|Met|Gly|Met|Asn|Arg|Lys|Ala|Ile|
| |195| | | | |200| | | |205| | | | | |
|Arg|Glu|Asp|Gly|Met|Pro|Gly|Gly|Arg|Asn|Lys|Ser|Ile|Gly|Pro|Val|
|210| | | | |215| | | |220| | | | | | |
|Gln|Ile|Ser|Glu|Glu|Glu|Ile|Glu|Arg|Ile|Met|Ser|Gly|Gln|Glu|Phe|
|225| | | |230| | | |235| | | | | | |240|
|Glu|Glu|Glu|Ala|Asn|His|Trp|Ser|Asn|His|Gly|Asp|Ser|Asp|His|Ser|
| | | |245| | | |250| | | |255| | | | |
|Ser|Pro|Gly|Asn|Arg|Ala|Ser|Glu|Ser|Asn|Gln|Pro|Ser|Pro|Gly|Ser|
| | |260| | | |265| | | |270| | | | | |
|Thr|Leu|Ser|Ser|Ser|Arg|Ser|Val|Glu|Leu|Asn|Gly|Phe|Met|Ala|Phe|
| |275| | | | |280| | | |285| | | | | |
|Arg|Asp|Gln|Tyr|Met|Gly|Met|Ser|Val|Pro|Pro|His|Tyr|Gln|Tyr|Ile|
|290| | | | |295| | | |300| | | | | | |
|Pro|His|Leu|Phe|Ser|Tyr|Ser|Gly|His|Ser|Pro|Leu|Leu|Pro|Pro|Gln|
|305| | | | |310| | | |315| | | | | |320|
|Ala|Arg|Ser|Leu|Asp|Pro|Gln|Ser|Tyr|Ser|Leu|Ile|His|Gln|Leu|Met|
| | | |325| | | |330| | | |335| | | | |
|Ser|Ala|Glu|Asp|Leu|Glu|Pro|Leu|Gly|Thr|Pro|Met|Leu|Ile|Glu|Asp|
| | |340| | | |345| | | |350| | | | | |
|Gly|Tyr|Ala|Val|Thr|Gln|Ala|Glu|Leu|Phe|Ala|Leu|Leu|Cys|Arg|Leu|
| |355| | | | |360| | | |365| | | | | |
|Ala|Asp|Glu|Leu|Leu|Phe|Arg|Gln|Ile|Ala|Trp|Ile|Lys|Lys|Leu|Pro|
|370| | | | |375| | | |380| | | | | | |
|Phe|Phe|Cys|Glu|Leu|Ser|Ile|Lys|Asp|Tyr|Thr|Cys|Leu|Leu|Ser|Ser|
|385| | | | |390| | | |395| | | | | |400|
|Thr|Trp|Gln|Glu|Leu|Ile|Leu|Leu|Ser|Ser|Leu|Thr|Val|Tyr|Ser|Lys|
| | | |405| | | |410| | | |415| | | | |
|Gln|Ile|Phe|Gly|Glu|Leu|Ala|Asp|Val|Thr|Ala|Lys|Tyr|Ser|Pro|Ser|
| | |420| | | |425| | | |430| | | | | |
|Asp|Glu|Glu|Leu|His|Arg|Phe|Ser|Asp|Glu|Gly|Met|Glu|Val|Ile|Glu|
| |435| | | | |440| | | |445| | | | | |
|Arg|Leu|Ile|Tyr|Leu|Tyr|His|Lys|Phe|His|Gln|Leu|Lys|Val|Ser|Asn|
|450| | | | |455| | | |460| | | | | | |
|Glu|Glu|Tyr|Ala|Cys|Met|Lys|Ala|Ile|Asn|Phe|Leu|Asn|Gln|Asp|Ile|
|465| | | |470| | | |475| | | | | | |480|
|Arg|Gly|Leu|Thr|Ser|Ala|Ser|Gln|Leu|Glu|Gln|Leu|Asn|Lys|Arg|Tyr|
| | | |485| | | |490| | | |495| | | | |
|Trp|Tyr|Ile|Cys|Gln|Asp|Phe|Thr|Glu|Tyr|Lys|Tyr|Thr|His|Gln|Pro|
| | |500| | | |505| | | |510| | | | | |
|Asn|Arg|Phe|Pro|Asp|Leu|Met|Met|Cys|Leu|Pro|Glu|Ile|Arg|Tyr|Ile|

```
                    515                    520                         525
Ala  Gly  Lys  Met  Val  Asn  Val  Pro  Leu  Glu  Gln  Leu  Pro  Leu  Leu  Phe
     530                    535                      540

Lys  Val  Val  Leu  His  Ser  Cys  Lys  Thr  Ser  Thr  Val  Lys  Glu
545                      550                      555
```

( 2 ) INFORMATION FOR SEQ ID NO:13:

( i ) SEQUENCE CHARACTERISTICS:
        ( A ) LENGTH: 2315 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR79 (XR79.SEQ)

( i x ) FEATURE:
        ( A ) NAME/KEY: CDS
        ( B ) LOCATION: 204..2009

( x i ) SEQUENCE DESCRIPTION: SEQ ID NO:13:

```
GCGTTAGAAA  AGGTTCAAAA  TAGGCACAAA  GTCGTGAAAA  TATCGTAACT  GACCGGAAGT    60

AACATAACTT  TAACCAAGTG  CCTCGAAAAA  TAGATGTTTT  TAAAAGCTCA  AGAATGGTGA    120

TAACAGACGT  CCAATAAGAA  TTTTCAAAGA  GCCAATTATT  TATACAGCCG  ACGACTATTT    180

TTTAGCCGCC  TGCTGTGGCG  ACA ATG GAC GGC GTT AAG GTT GAG ACG TTC            230
                           Met Asp Gly Val Lys Val Glu Thr Phe
                            1               5

ATC AAA AGC GAA GAA AAC CGA GCG ATG CCC TTG ATC GGA GGA GGC AGT           278
Ile Lys Ser Glu Glu Asn Arg Ala Met Pro Leu Ile Gly Gly Gly Ser
 10               15                  20                  25

GCC TCA GGC GGC ACT CCT CTG CCA GGA GGC GGC GTG GGA ATG GGA GCC           326
Ala Ser Gly Gly Thr Pro Leu Pro Gly Gly Gly Val Gly Met Gly Ala
                 30                  35                  40

GGA GCA TCC GCA ACG TTG AGC GTG GAG CTG TGT TTG GTG TGC GGG GAC           374
Gly Ala Ser Ala Thr Leu Ser Val Glu Leu Cys Leu Val Cys Gly Asp
             45                  50                  55

CGC GCC TCC GGG CGG CAC TAC GGA GCC ATA AGC TGC GAA GGC TGC AAG           422
Arg Ala Ser Gly Arg His Tyr Gly Ala Ile Ser Cys Glu Gly Cys Lys
         60                  65                  70

GGA TTC TTC AAG CGC TCG ATC CGG AAG CAG CTG GGC TAC CAG TGT CGC           470
Gly Phe Phe Lys Arg Ser Ile Arg Lys Gln Leu Gly Tyr Gln Cys Arg
     75                  80                  85

GGG GCT ATG AAC TGC GAG GTC ACC AAG CAC CAC AGG AAT CGG TGC CAG           518
Gly Ala Met Asn Cys Glu Val Thr Lys His His Arg Asn Arg Cys Gln
 90                  95                 100                 105

TTC TGT CGA CTA CAG AAG TGC CTG GCC AGC GGC ATG CGA AGT GAT TCT           566
Phe Cys Arg Leu Gln Lys Cys Leu Ala Ser Gly Met Arg Ser Asp Ser
                110                 115                 120

GTG CAG CAC GAG AGG AAA CCG ATT GTG GAC AGG AAG GAG GGG ATC ATC           614
Val Gln His Glu Arg Lys Pro Ile Val Asp Arg Lys Glu Gly Ile Ile
            125                 130                 135

GCT GCT GCC GGT AGC TCA TCC ACT TCT GGC GGT AAT GGC TCG TCC               662
Ala Ala Ala Gly Ser Ser Ser Thr Ser Gly Gly Gly Asn Gly Ser Ser
        140                 145                 150

ACC TAC CTA TCC GGC AAG TCC GGC TAT CAG CAG GGG CGT GGC AAG GGG           710
Thr Tyr Leu Ser Gly Lys Ser Gly Tyr Gln Gln Gly Arg Gly Lys Gly
    155                 160                 165

CAC AGT GTA AAG GCC GAA TCC GCG CCA CGC CTC CAG TGC ACA GCG CGC           758
His Ser Val Lys Ala Glu Ser Ala Pro Arg Leu Gln Cys Thr Ala Arg
```

-continued

| 170 | | | | 175 | | | | 180 | | | | 185 | | | | |
|---|---|---|---|---|---|---|---|---|---|---|---|---|---|---|---|---|
| CAG | CAA | CGG | GCC | TTC | AAT | TTG | AAT | GCA | GAA | TAT | ATT | CCG | ATG | GGT | TTG | 806 |
| Gln | Gln | Arg | Ala | Phe | Asn | Leu | Asn | Ala | Glu | Tyr | Ile | Pro | Met | Gly | Leu | |
| | | | | 190 | | | | | 195 | | | | | 200 | | |
| AAT | TTC | GCA | GAA | CTA | ACG | CAG | ACA | TTG | ATG | TTC | GCT | ACC | CAA | CAG | CAG | 854 |
| Asn | Phe | Ala | Glu | Leu | Thr | Gln | Thr | Leu | Met | Phe | Ala | Thr | Gln | Gln | Gln | |
| | | | | | 205 | | | | | 210 | | | | | 215 | |
| CAG | CAA | CAA | CAG | CAA | CAG | CAT | CAA | CAG | AGT | GGT | AGC | TAT | TCG | CCA | GAT | 902 |
| Gln | Gln | Gln | Gln | Gln | Gln | His | Gln | Gln | Ser | Gly | Ser | Tyr | Ser | Pro | Asp | |
| | | | | 220 | | | | | 225 | | | | | 230 | | |
| ATT | CCG | AAG | GCA | GAT | CCC | GAG | GAT | GAC | GAG | GAC | GAC | TCA | ATG | GAC | AAC | 950 |
| Ile | Pro | Lys | Ala | Asp | Pro | Glu | Asp | Asp | Glu | Asp | Asp | Ser | Met | Asp | Asn | |
| | | 235 | | | | | 240 | | | | | 245 | | | | |
| AGC | AGC | ACG | CTG | TGC | TTG | CAG | TTG | CTC | GCC | AAC | AGC | GCC | AGC | AAC | AAC | 998 |
| Ser | Ser | Thr | Leu | Cys | Leu | Gln | Leu | Leu | Ala | Asn | Ser | Ala | Ser | Asn | Asn | |
| 250 | | | | | 255 | | | | | 260 | | | | | 265 | |
| AAC | TCG | CAG | CAC | CTG | AAC | TTT | AAT | GCT | GGG | GAA | GTA | CCC | ACC | GCT | CTG | 1046 |
| Asn | Ser | Gln | His | Leu | Asn | Phe | Asn | Ala | Gly | Glu | Val | Pro | Thr | Ala | Leu | |
| | | | | 270 | | | | | 275 | | | | | 280 | | |
| CCT | ACC | ACC | TCG | ACA | ATG | GGG | CTT | ATT | CAG | AGT | TCG | CTG | GAC | ATG | CGG | 1094 |
| Pro | Thr | Thr | Ser | Thr | Met | Gly | Leu | Ile | Gln | Ser | Ser | Leu | Asp | Met | Arg | |
| | | | 285 | | | | | 290 | | | | | 295 | | | |
| GTC | ATC | CAC | AAG | GGA | CTG | CAG | ATC | CTG | CAG | CCC | ATC | CAA | AAC | CAA | CTG | 1142 |
| Val | Ile | His | Lys | Gly | Leu | Gln | Ile | Leu | Gln | Pro | Ile | Gln | Asn | Gln | Leu | |
| | | 300 | | | | | 305 | | | | | 310 | | | | |
| GAG | CGA | AAT | GGT | AAT | CTG | AGT | GTG | AAG | CCC | GAG | TGC | GAT | TCA | GAG | GCG | 1190 |
| Glu | Arg | Asn | Gly | Asn | Leu | Ser | Val | Lys | Pro | Glu | Cys | Asp | Ser | Glu | Ala | |
| | 315 | | | | | 320 | | | | | 325 | | | | | |
| GAG | GAC | AGT | GGC | ACC | GAG | GAT | GCC | GTA | GAC | GCG | GAG | CTG | GAG | CAC | ATG | 1238 |
| Glu | Asp | Ser | Gly | Thr | Glu | Asp | Ala | Val | Asp | Ala | Glu | Leu | Glu | His | Met | |
| 330 | | | | | 335 | | | | | 340 | | | | | 345 | |
| GAA | CTA | GAC | TTT | GAG | TGC | GGT | GGG | AAC | CGA | AGC | GGT | GGA | AGC | GAT | TTT | 1286 |
| Glu | Leu | Asp | Phe | Glu | Cys | Gly | Gly | Asn | Arg | Ser | Gly | Gly | Ser | Asp | Phe | |
| | | | | 350 | | | | | 355 | | | | | 360 | | |
| GCT | ATC | AAT | GAG | GCG | GTC | TTT | GAA | CAG | GAT | CTT | CTC | ACC | GAT | GTG | CAG | 1334 |
| Ala | Ile | Asn | Glu | Ala | Val | Phe | Glu | Gln | Asp | Leu | Leu | Thr | Asp | Val | Gln | |
| | | | 365 | | | | | 370 | | | | | 375 | | | |
| TGT | GCC | TTT | CAT | GTG | CAA | CCG | CCG | ACT | TTG | GTC | CAC | TCG | TAT | TTA | AAT | 1382 |
| Cys | Ala | Phe | His | Val | Gln | Pro | Pro | Thr | Leu | Val | His | Ser | Tyr | Leu | Asn | |
| | | 380 | | | | | 385 | | | | | 390 | | | | |
| ATT | CAT | TAT | GTG | TGT | GAG | ACG | GGC | TCG | CGA | ATC | ATT | TTT | CTC | ACC | ATC | 1430 |
| Ile | His | Tyr | Val | Cys | Glu | Thr | Gly | Ser | Arg | Ile | Ile | Phe | Leu | Thr | Ile | |
| | 395 | | | | | 400 | | | | | 405 | | | | | |
| CAT | ACC | CTT | CGA | AAG | GTT | CCA | GTT | TTC | GAA | CAA | TTG | GAA | GCC | CAT | ACA | 1478 |
| His | Thr | Leu | Arg | Lys | Val | Pro | Val | Phe | Glu | Gln | Leu | Glu | Ala | His | Thr | |
| 410 | | | | | 415 | | | | | 420 | | | | | 425 | |
| CAG | GTG | AAA | CTC | CTG | AGA | GGA | GTG | TGG | CCA | GCA | TTA | ATG | GCT | ATA | GCT | 1526 |
| Gln | Val | Lys | Leu | Leu | Arg | Gly | Val | Trp | Pro | Ala | Leu | Met | Ala | Ile | Ala | |
| | | | | 430 | | | | | 435 | | | | | 440 | | |
| TTG | GCG | CAG | TGT | CAG | GGT | CAG | CTT | TCG | GTG | CCC | ACC | ATT | ATC | GGG | CAG | 1574 |
| Leu | Ala | Gln | Cys | Gln | Gly | Gln | Leu | Ser | Val | Pro | Thr | Ile | Ile | Gly | Gln | |
| | | | 445 | | | | | 450 | | | | | 455 | | | |
| TTT | ATT | CAA | AGC | ACT | CGC | CAG | CTA | GCG | GAT | ATC | GAT | AAG | ATC | GAA | CCG | 1622 |
| Phe | Ile | Gln | Ser | Thr | Arg | Gln | Leu | Ala | Asp | Ile | Asp | Lys | Ile | Glu | Pro | |
| | | 460 | | | | | 465 | | | | | 470 | | | | |
| TTG | AAG | ATC | TCG | AAG | ATG | GCA | AAT | CTC | ACC | AGG | ACC | CTG | CAC | GAC | TTT | 1670 |
| Leu | Lys | Ile | Ser | Lys | Met | Ala | Asn | Leu | Thr | Arg | Thr | Leu | His | Asp | Phe | |
| | 475 | | | | | 480 | | | | | 485 | | | | | |
| GTC | CAG | GAG | CTC | CAG | TCA | CTG | GAT | GTT | ACT | GAT | ATG | GAG | TTT | GGC | TTG | 1718 |
| Val | Gln | Glu | Leu | Gln | Ser | Leu | Asp | Val | Thr | Asp | Met | Glu | Phe | Gly | Leu | |

|  |  |  |  |  |  |  |  |  |  |  |  |  |  |  |  |
|---|---|---|---|---|---|---|---|---|---|---|---|---|---|---|---|

```
              490                 495                  500                  505
         CTG  CGT  CTG  ATC  TTG  CTC  TTC  AAT  CCA  ACG  CTC  TTC  CAG  CAT  CGC  AAG    1766
         Leu  Arg  Leu  Ile  Leu  Leu  Phe  Asn  Pro  Thr  Leu  Phe  Gln  His  Arg  Lys
                        510                      515                      520

GAG  CGG  TCG  TTG  CGA  GGC  TAC  GTC  CGC  AGA  GTC  CAA  CTC  TAC  GCT  CTG    1814
         Glu  Arg  Ser  Leu  Arg  Gly  Tyr  Val  Arg  Arg  Val  Gln  Leu  Tyr  Ala  Leu
                        525                      530                      535

TCA  AGT  TTG  AGA  AGG  CAG  GGT  GGC  ATC  GGC  GGC  GGC  GAG  GAG  CGC  TTT    1862
         Ser  Ser  Leu  Arg  Arg  Gln  Gly  Gly  Ile  Gly  Gly  Gly  Glu  Glu  Arg  Phe
                        540                      545                      550

AAT  GTT  CTG  GTG  GCT  CGC  CTT  CTT  CCG  CTC  AGC  AGC  CTG  GAC  GCA  GAG    1910
         Asn  Val  Leu  Val  Ala  Arg  Leu  Leu  Pro  Leu  Ser  Ser  Leu  Asp  Ala  Glu
              555                      560                      565

GCC  ATG  GAG  GAG  CTG  TTC  TTC  GCC  AAC  TTG  GTG  GGG  CAG  ATG  CAG  ATG    1958
         Ala  Met  Glu  Glu  Leu  Phe  Phe  Ala  Asn  Leu  Val  Gly  Gln  Met  Gln  Met
         570                      575                      580                      585

GAT  GCT  CTT  ATT  CCG  TTC  ATA  CTG  ATG  ACC  AGC  AAC  ACC  AGT  GGA  CTG    2006
         Asp  Ala  Leu  Ile  Pro  Phe  Ile  Leu  Met  Thr  Ser  Asn  Thr  Ser  Gly  Leu
                        590                      595                      600

TAGGCGGAAT TGAGAAGAAC AGGGCGCAAG CAGATTCGCT AGACTGCCCA AAAGCAAGAC                 2066
         TGAAGATGGA CCAAGTGCGG GCAATACATG TAGCAACTAG GCAAATCCCA TTAATTATAT                 2126
         ATTTAATATA TACAATATAT AGTTTAGGAT ACAATATTCT AACATAAAAC CATGAGTTTA                 2186
         TTGTTGTTCA CAGATAAAAT GGAATCGATT TCCCAATAAA AGCGAATATG TTTTTAAACA                 2246
         GAATGTTTGC ATCAGAACTT TGAGATGTAT ACATTAGATT ATTACAACAC AAAAAAAAA                  2306
         AAAAAAAA                                                                         2315
```

( 2 ) INFORMATION FOR SEQ ID NO:14:

( i ) SEQUENCE CHARACTERISTICS:
        ( A ) LENGTH: 601 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met  Asp  Gly  Val  Lys  Val  Glu  Thr  Phe  Ile  Lys  Ser  Glu  Glu  Asn  Arg
  1              5                       10                       15

Ala  Met  Pro  Leu  Ile  Gly  Gly  Gly  Ser  Ala  Ser  Gly  Gly  Thr  Pro  Leu
               20                       25                       30

Pro  Gly  Gly  Gly  Val  Gly  Met  Gly  Ala  Gly  Ala  Ser  Ala  Thr  Leu  Ser
               35                       40                       45

Val  Glu  Leu  Cys  Leu  Val  Cys  Gly  Asp  Arg  Ala  Ser  Gly  Arg  His  Tyr
          50                       55                       60

Gly  Ala  Ile  Ser  Cys  Glu  Gly  Cys  Lys  Gly  Phe  Phe  Lys  Arg  Ser  Ile
 65                       70                       75                       80

Arg  Lys  Gln  Leu  Gly  Tyr  Gln  Cys  Arg  Gly  Ala  Met  Asn  Cys  Glu  Val
                    85                       90                       95

Thr  Lys  His  His  Arg  Asn  Arg  Cys  Gln  Phe  Cys  Arg  Leu  Gln  Lys  Cys
              100                      105                      110

Leu  Ala  Ser  Gly  Met  Arg  Ser  Asp  Ser  Val  Gln  His  Glu  Arg  Lys  Pro
              115                      120                      125

Ile  Val  Asp  Arg  Lys  Glu  Gly  Ile  Ile  Ala  Ala  Ala  Gly  Ser  Ser  Ser
         130                      135                      140

Thr  Ser  Gly  Gly  Gly  Asn  Gly  Ser  Ser  Thr  Tyr  Leu  Ser  Gly  Lys  Ser
145                       150                      155                      160
```

-continued

| | | | | | | | | | | | | | | |
|---|---|---|---|---|---|---|---|---|---|---|---|---|---|---|
| Gly | Tyr | Gln | Gln | Gly<br>165 | Arg | Gly | Lys | Gly | His<br>170 | Ser | Val | Lys | Ala | Glu<br>175 | Ser |
| Ala | Pro | Arg | Leu<br>180 | Gln | Cys | Thr | Ala | Arg<br>185 | Gln | Gln | Arg | Ala | Phe<br>190 | Asn | Leu |
| Asn | Ala | Glu<br>195 | Tyr | Ile | Pro | Met | Gly<br>200 | Leu | Asn | Phe | Ala | Glu<br>205 | Leu | Thr | Gln |
| Thr | Leu<br>210 | Met | Phe | Ala | Thr | Gln<br>215 | Gln | Gln | Gln | Gln | Gln<br>220 | Gln | Gln | Gln | His |
| Gln<br>225 | Gln | Ser | Gly | Ser | Tyr<br>230 | Ser | Pro | Asp | Ile | Pro<br>235 | Lys | Ala | Asp | Pro | Glu<br>240 |
| Asp | Asp | Glu | Asp | Asp<br>245 | Ser | Met | Asp | Asn | Ser<br>250 | Ser | Thr | Leu | Cys | Leu<br>255 | Gln |
| Leu | Leu | Ala | Asn<br>260 | Ser | Ala | Ser | Asn | Asn<br>265 | Asn | Ser | Gln | His | Leu<br>270 | Asn | Phe |
| Asn | Ala | Gly<br>275 | Glu | Val | Pro | Thr | Ala<br>280 | Leu | Pro | Thr | Thr | Ser<br>285 | Thr | Met | Gly |
| Leu | Ile<br>290 | Gln | Ser | Ser | Leu | Asp<br>295 | Met | Arg | Val | Ile | His<br>300 | Lys | Gly | Leu | Gln |
| Ile<br>305 | Leu | Gln | Pro | Ile | Gln<br>310 | Asn | Gln | Leu | Glu | Arg<br>315 | Asn | Gly | Asn | Leu | Ser<br>320 |
| Val | Lys | Pro | Glu | Cys<br>325 | Asp | Ser | Glu | Ala | Glu<br>330 | Asp | Ser | Gly | Thr | Glu<br>335 | Asp |
| Ala | Val | Asp | Ala<br>340 | Glu | Leu | Glu | His | Met<br>345 | Glu | Leu | Asp | Phe | Glu<br>350 | Cys | Gly |
| Gly | Asn | Arg<br>355 | Ser | Gly | Gly | Ser | Asp<br>360 | Phe | Ala | Ile | Asn | Glu<br>365 | Ala | Val | Phe |
| Glu | Gln<br>370 | Asp | Leu | Leu | Thr | Asp<br>375 | Val | Gln | Cys | Ala | Phe<br>380 | His | Val | Gln | Pro |
| Pro<br>385 | Thr | Leu | Val | His | Ser<br>390 | Tyr | Leu | Asn | Ile | His<br>395 | Tyr | Val | Cys | Glu | Thr<br>400 |
| Gly | Ser | Arg | Ile | Ile<br>405 | Phe | Leu | Thr | Ile | His<br>410 | Thr | Leu | Arg | Lys | Val<br>415 | Pro |
| Val | Phe | Glu | Gln<br>420 | Leu | Glu | Ala | His | Thr<br>425 | Gln | Val | Lys | Leu | Leu<br>430 | Arg | Gly |
| Val | Trp | Pro<br>435 | Ala | Leu | Met | Ala | Ile<br>440 | Ala | Leu | Ala | Gln | Cys<br>445 | Gln | Gly | Gln |
| Leu | Ser<br>450 | Val | Pro | Thr | Ile | Ile<br>455 | Gly | Gln | Phe | Ile | Gln<br>460 | Ser | Thr | Arg | Gln |
| Leu<br>465 | Ala | Asp | Ile | Asp | Lys<br>470 | Ile | Glu | Pro | Leu | Lys<br>475 | Ile | Ser | Lys | Met | Ala<br>480 |
| Asn | Leu | Thr | Arg | Thr<br>485 | Leu | His | Asp | Phe | Val<br>490 | Gln | Glu | Leu | Gln | Ser<br>495 | Leu |
| Asp | Val | Thr | Asp<br>500 | Met | Glu | Phe | Gly | Leu<br>505 | Leu | Arg | Leu | Ile | Leu<br>510 | Leu | Phe |
| Asn | Pro | Thr<br>515 | Leu | Phe | Gln | His | Arg<br>520 | Lys | Glu | Arg | Ser | Leu<br>525 | Arg | Gly | Tyr |
| Val | Arg<br>530 | Arg | Val | Gln | Leu | Tyr<br>535 | Ala | Leu | Ser | Ser | Leu<br>540 | Arg | Arg | Gln | Gly |
| Gly<br>545 | Ile | Gly | Gly | Gly | Glu<br>550 | Glu | Arg | Phe | Asn | Val<br>555 | Leu | Val | Ala | Arg | Leu<br>560 |
| Leu | Pro | Leu | Ser | Ser<br>565 | Leu | Asp | Ala | Glu | Ala<br>570 | Met | Glu | Glu | Leu | Phe<br>575 | Phe |
| Ala | Asn | Leu | Val<br>580 | Gly | Gln | Met | Gln | Met<br>585 | Asp | Ala | Leu | Ile | Pro<br>590 | Phe | Ile |

```
Leu Met Thr Ser Asn Thr Ser Gly Leu
        595                 600
```